(12) United States Patent
Musumeci et al.

(10) Patent No.: US 9,920,039 B2
(45) Date of Patent: *Mar. 20, 2018

(54) 1,2,4-OXADIAZOL COMPOUNDS ACTIVE AGAINST GRAM-POSITIVE PATHOGENS

(71) Applicants: UNIVERSITÀ DEGLI STUDI DI MILANO—BICOCCA, Milan (IT); ISTITUTO EURO MEDITERRANEO DI SCIENZA E TECNOLOGIA, Palermo (IT)

(72) Inventors: Rosario Musumeci, Giarre (IT); Clementina Elvezia Anna Cocuzza, Milan (IT); Cosimo Gianluca Fortuna, Catania (IT); Andrea Pace, Palermo (IT); Antonio Palumbo Piccionello, Santa Flavia (IT)

(73) Assignees: UNIVERSITÀ DEGLI STUDI DI MILANO—BICOCCA, Milan (IT); ISTITUTO EURO MEDITERRANEO DI SCIENZA E TECNOLOGIA, Palermo (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/777,508

(22) PCT Filed: Mar. 17, 2014

(86) PCT No.: PCT/IB2014/059896
§ 371 (c)(1),
(2) Date: Sep. 15, 2015

(87) PCT Pub. No.: WO2014/141218
PCT Pub. Date: Sep. 18, 2014

(65) Prior Publication Data
US 2016/0297807 A1    Oct. 13, 2016

Related U.S. Application Data

(63) Continuation-in-part of application No. 13/839,485, filed on Mar. 15, 2013, now Pat. No. 9,862,710.

(30) Foreign Application Priority Data

Mar. 15, 2013   (IT) .............................. RM2013A0155

(51) Int. Cl.
*C07D 413/10*   (2006.01)
*C07D 413/14*   (2006.01)

(52) U.S. Cl.
CPC ......... *C07D 413/10* (2013.01); *C07D 413/14* (2013.01)

(58) Field of Classification Search
CPC ........................... C07D 413/10; C07D 413/14
See application file for complete search history.

(56) References Cited

U.S. PATENT DOCUMENTS

| 4,948,801 A | 8/1990 | Carlson et al. | |
| 5,977,373 A * | 11/1999 | Gadwood | C07D 417/10 548/128 |
| 7,838,532 B2 * | 11/2010 | Surber | A61K 9/0075 424/405 |
| 2005/0043374 A1 | 2/2005 | Gravestock | |
| 2008/0146573 A1 * | 6/2008 | Gant | C07D 263/20 514/236.8 |

FOREIGN PATENT DOCUMENTS

| EP | 0 325 781 | 1/1990 |
| EP | 0 352 781 | 1/1990 |
| WO | 99/02525 | 1/1999 |
| WO | 03/035648 | 5/2003 |

OTHER PUBLICATIONS

International Search Report for PCT/IB2014/059896, three pages, dated May 22, 2014.
Written Opinion of the ISA for PCT/IB2014/059896, five pages, dated May 22, 2014.
Hauck et al. "New carbon-linked azole oxazolidinones with improved potency and pharmacokinetics" *Bioorganic & Medicinal Chemistry Letters* 17:337-340 (2007).
Thomasco et al. "The synthesis and antibacterial activity of 1,3,4-thiadiazole phenyl oxazolidione analogues" *Bioorganic & Medicinal Chemistry Letters* 13:4193-4196 (2003).

* cited by examiner

*Primary Examiner* — Uma Ramachandran
(74) *Attorney, Agent, or Firm* — Nixon & Vanderhye PC

(57) ABSTRACT

The present invention relates to new oxazolidinone compounds of general formula (I) having antibiotic activity even against multiresistant bacterial strains (I).

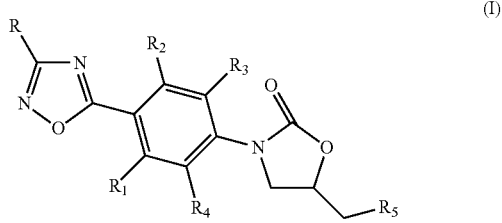

12 Claims, 6 Drawing Sheets

SCHEME 1

SCHEME 2

SCHEME 3

1,2,4-OXADIAZOL COMPOUNDS ACTIVE AGAINST GRAM-POSITIVE PATHOGENS

This application is the U.S. national phase of International Application No. PCT/IB2014/059896, filed 14 Mar. 2014, which designated the U.S. and claims priority benefit of applications U.S. Ser. No. 13/839,485, filed 15 Mar. 2013, and IT RM2013A000155, filed 15 Mar. 2013; the entire contents of each of which are hereby incorporated by reference.

STATE OF THE PRIOR ART

Use and misuse of antibacterial agents have resulted in the development of bacterial resistance to all antibiotics in clinical use, irrespective of the chemical class or molecular target of the drug. Infections caused by multiresistant Gram-positive cocci, such as methicillin-resistant *Staphylococcus aureus* (MRSA), vancomycin-resistant enterococci (VRE) and penicillin-resistant *Streptococcus pneumoniae* (PNSSP), have emerged as major public health concern, both in hospital and community settings worldwide. The need for new antibiotics urged the Infectious Disease Society of America (IDSA) to issue the challenge to develop ten new antibiotics by 2020.

Oxazolidinones are a class of antibacterial agents which displayed activity against a variety of Gram-positive pathogens and are highly potent against multidrug-resistant bacteria. In particular, oxazolidinones are used to treat skin and respiratory tract infections caused by *Staphylococcus aureus* and streptococci strains, as well as being active against vancomycin-resistant *Enterococcus faecium*. Linezolid (FIG. 1), the first oxazolidinone antibiotic approved for clinical use, has been shown to inhibit translation at the initiation phase of protein synthesis in bacteria by binding to the 50S ribosomal subunit. Since 2001, however, linezolid resistance began to appear in *Staphylococcus aureus* and *Enterococcus faecium* clinical isolates and the rate of resistance raised especially among enterococci and *Staphylococcus epidermidis* strains with its usage.[1-4] In addition, linezolid therapy is not without side effects such as reversible myelosuppression and inhibition of monoamine oxidases (MAO).

A number of solutions to the problem of bacterial resistance are possible. Successful strategies include combination of existing antibacterial agents with other drugs as well as the development of improved diagnostic procedures that may lead to rapid identification of the causative pathogen and permit the use of antibacterial agents with a narrow spectrum of activity. Another strategy is the discovery of novel classes of antibacterial agents acting through new mechanisms of action. However, the most common approach, and still the most promising one, is the modification of existing classes of antibacterial agents to provide new analogues with improved activities, although activity and toxicity of the new analogues are not easily predictable.

In this context, many researchers have attempted to modify, without even obtaining results such as to lead to approval for use of new molecules, the structure of linezolid to improve the antibacterial activity. In order to rationalize the site of modifications, the structure of linezolid can formally be divided into four portions according to oxazolidinone antibacterials nomenclature[5]: i) the A-ring, consisting of the oxazolidinone central heterocycle; ii) the B-ring, consisting of a N-aryl moiety linked to the oxazolidinone nitrogen; iii) the C-ring, consisting of a carboheterocyclic functional group, not necessarily aromatic; iv) the side-chain, consisting of any functional group linked to the oxazolidinone C(5) or in an isosteric position with respect to an A-ring of general type (FIG. 1).

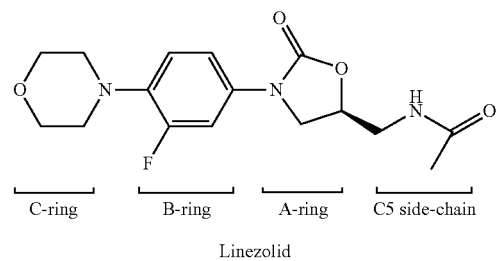

FIG. 1

Linezolid

Different types of modifications are reported in literature; the most common one regards the C-ring, while only few modifications were reported for the A-ring, and in some cases good activity was retained.[6-7]

Our group previously reported that the replacement of the oxazolidinone (A-ring) with an isosteric 1,2,4-oxadiazole heteroaromatic ring resulted in a lack of activity.[8] Therefore, these compounds have been chosen as references for inactive linezolid-like compounds in a virtual screening approach.

The purpose of the present invention is to find new molecules suitable as medicaments which exceed the limits and disadvantages of the prior art molecules, in terms of antibacterial activity, especially against resistant strains, and harmlessness.

SUMMARY OF THE INVENTION

The present invention is based on the discovery that the substitution of the C-ring of linezolid-like molecules, with a five-membered heterocyclic ring, also substituted, containing 2 or 3 heteroatoms, is effective for the obtainment of new oxazolidinone antibiotics with a tunable activity by the presence of further modifications at the B-ring and at the C(5) side-chain of the oxazolidinone nucleus.

Therefore, objects of the present invention are new compounds with a general formula (I), and their use for the treatment of infections preferably caused by Gram-positive bacteria,

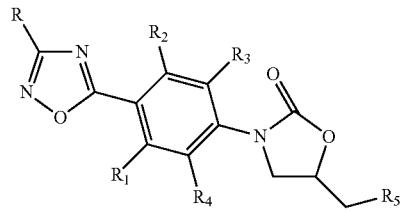

Formula (I)

as racemic mixtures or pure enantiomers or mixtures enriched with one of the S or R enantiomers where:

R=, F, Cl, Br, I, (C1-C3) alkyl (methyl, ethyl, n-propyl, iso-propyl), (C3-C6) cyclo-alkyl, phenyl, aryl, heteroaryl, $NH_2$, OH, SH, $NHR_6$, $N(R_6)_2$, $OR_6$ with $R_6$=(C1-C3) alkyl, (C3-C6) cyclo-alkyl, aryl, heteroaryl, (C1-C4) acyl;

$R_{1-4}$= independently H, F, Cl, Br, $CH_3$, OH, $OCH_3$;

$R_5$=—$NH_2$; —I; —$N_3$; —OH; —NCH, —NCH(X)$CH_3$ with X=O or S; —NHC(X)$CH_2$Z with X=O, X, Z=F, Cl; —NHC(X)$CHZ_2$ with X=O, S, Z=F, Cl; —NHC(X)$CZ_3$ with X=O, S, Z=F, Cl; —NHC(X)$NHR_7$ with X=O, R, $R_7$=H, (C1-C3) alkyl, (C3-C6) cycloalkyl, aryl, heteroaryl, (C1-C3) acyl.

Specific embodiment of the invention consists on compounds with general formula (I) where R is methyl, ethyl, n-propyl, iso-propyl;

or compounds with general formula (I) where at least one between $R_1$, $R_2$, $R_3$ or $R_4$ is a fluorine atom, while the other are H;

or compounds with general formula (I) where $R_5$ is selected between: —NHC(=O)CH$_3$, —NHC(=S)CH$_3$, —NHC(=O)CH$_2$F, —NHC(=)CH$_2$F, —NHC(=)CH$_2$Cl, —NHC(=S)CH$_2$Cl, —NHC(=S)NH$_2$, NHC(=O)NH$_2$, —NHC(=O)NHCH$_3$, —NHC(=S)NHCH$_3$, —NHC(=O)NHC$_2$H$_5$, —NHC(=S)NHC$_2$H$_5$, —NCS; 1,2,3-triazol-1-yl;

or compounds with general formula (I) where R is a methyl and $R_5$ is selected between: —NHC(=O)CH$_3$, —NHC(=S)CH$_3$, —NHC(=O)CH$_2$F, —NHC(=S)CH$_2$F, —NHC(=O)CH$_2$Cl, —NHC(=S)CH$_2$Cl, —NHC(=S)NH$_2$, NHC(=O)NH$_2$, —NHC(=O)NHCH$_3$, —NHC(=S)NHCH$_3$, —NHC(=O)NHC$_2$H$_5$, —NHC(=S)NHC$_2$H$_5$; —NCS; 1,2,3-triazol-1-yl;

or compounds with general formula (I) where $R_1$ is F, $R_2$, $R_3$ and $R_4$ are H and R is a methyl and $R_5$ is selected between: —NHC(=O)CH$_3$, —NHC(=S)CH$_3$, —NHC(=O)CH$_2$F, —NHC(=S)CH$_2$F, —NHC(=O)CH$_2$Cl, —NHC(=S)CH$_2$Cl, —NHC(=S)NH$_2$, NHC(=O)NH$_2$, —NHC(=O)NHCH$_3$, —NHC(=S)NHCH$_3$, —NHC(=O)NHC$_2$H$_5$, —NHC(=S)NHC$_2$H$_5$, —NCS; 1,2,3 triazol-1-yl.

In a preferred embodiment of the invention, all compounds indicated above are pure S enantiomer or in a mixture enriched with the S enantiomer.

In a further embodiment of the invention the claimed compounds are intended for use in the treatment of infections caused by Gram-positive bacteria, preferably multi-antibiotic resistant (also called multi-resistant), for example in the treatment of infections caused by *Staphylococcus* spp, *Enterococcus* spp, *Streptococcus* spp, in particular of infection caused by *Staphylococcus aureus, Staphylococcus epidermidis, Staphylococcus hominis, Enterococcus faecium, Enterococcus faecalis, Streptococcus pneumoniae*. Especially if resistant to one or more of the antibiotics methicillin, vancomycin, penicillin, macrolides, fluoroquinolones and linezolid.

A second object of the invention are pharmaceutical compositions comprising the compounds of the invention as active ingredients and a pharmaceutically acceptable excipient.

Such compositions are intended for use in the treatment of infections by both Gram-positive and Gram-negative bacteria including multi-resistant strains.

A third object of the invention are processes for preparing the compounds of the invention which comprises the steps shown in diagrams 1, 2 and 3.

In one embodiment of the invention the methods comprise one or more steps of separation of the enantiomers S and R or enrichment of the racemic mixture in one of the enantiomers, preferably the S enantiomer.

A fourth object of the invention are processes for the preparation of pharmaceutical compositions comprising the step of mixing the active ingredients with a pharmacologically acceptable excipient.

A further object of the invention is the use of the compounds of the invention for the preparation of a medicament for the treatment of infections by multi-resistant Gram-positive strains.

Advantages offered by the present invention reside in obtaining new antibiotic compounds with activity equivalent to or comparable to that of linezolid against linezolid-susceptible bacterial strains but with greater effectiveness than linezolid against bacterial strains resistant to linezolid and/or to other antibiotics. In addition some of these substances possess cytotoxicity levels comparable to or less than that of linezolid. Finally, replacing the morpholine ring of linezolid with the oxadiazole ring, as described herein, prevents the opening of the ring and the formation of inactive metabolites such as PNU-142586 and PNU-142300.

DETAILED DESCRIPTION OF THE INVENTION

Figure 1:
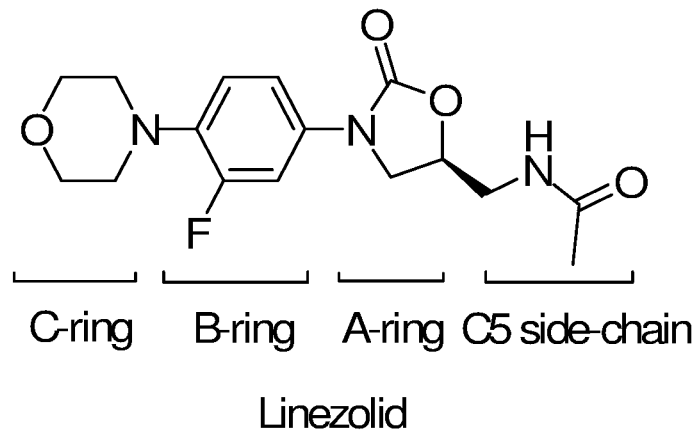
FIG. 1. Formula of linezolid with structural elements that compose it and nomenclature.

Compounds:

The chemical structure of the compounds of the present invention [formulas (I)] consists of an oxazolidinone ring (ring A), a phenyl ring (ring B), an oxadiazole ring (ring C) and a side-chain linked to the C5 position of the oxazolidinone (C5-linked side-chain).

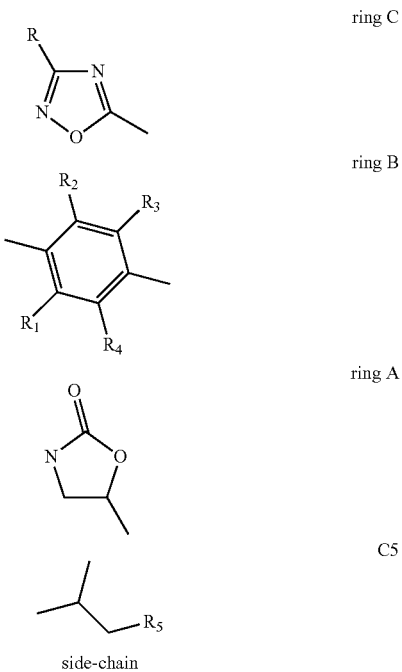

Ring C

The ring C is an 1,2,4-ossadiazole heterocycle linked via the C (5) to the ring B. The R substituent on the ring C can be a substituent chosen among: F, Cl, Br, I, methyl, ethyl, n-propyl, isopropyl, n-butyl, sec-butyl, ter-butyl, cyclopropyl, cyclobutyl, cyclopentyl, cyclohexyl, phenyl, aryl, heteroaryl, —NH$_2$, NHCH$_3$, NHC$_2$H$_5$, —N(CH$_3$)$_2$, N(CH$_3$)(C$_2$H$_5$), —NC(=O)CH$_3$, —NC(=O)C$_2$H$_5$, —NH(cyclopropyl), NH(cyclobutyl), NH(cyclopentyl), NH(cyclohexyl), —OH, —OCH$_3$, —OC$_2$H$_5$, —On-Propyl, Oi-Propyl, —SH, SCH$_3$.

Ring B

Groups R$_1$, R$_2$, R$_3$, R$_4$ are, independently from each other, H, F, Cl, Br, CH$_3$, OH, OCH$_3$. At least one of them is an halogen atom, for example R$_1$ is F, Cl, or Br, or R$_1$ and R$_2$ are F, Cl, or Br, or R$_1$, R$_2$, and R$_3$ are F or Cl. In a specific embodiment the halogen atom is F and the remaining R groups are hydrogen atoms. In a preferred formula, either R$_1$ or R$_2$ are F and R$_3$ and R$_4$ are H.

C5 Side-Chain

The R$_5$ substituent in the C5 side-chain linked at the position 5 of the oxazolidinone nucleus is chosen within a group comprising the following radicals: I, —N$_3$, —NHC(=O)CH$_3$, —NHC(=S)CH$_3$, —NHC(=O)CH$_2$F, —NHC(=S)CH$_2$F, —NHC(=O)CH$_2$Cl, —NHC(=S)CH$_2$Cl, —NHC(=O)CH$_2$Br, —NHC(=S)CH$_2$Br, —NHC(=O)CHF$_2$, —NHC(=S)CHF$_2$, —NHC(=O)CHCl$_2$, —NHC(=S)CHCl$_2$, —NHC(=O)CHBr$_2$, —NHC(=S)CHBr$_2$, —NHC(=O)CF$_3$, —NHC(=S)CF$_3$, —NHC(=O)CCl$_3$, —NHC(=S)CCl$_3$, —NHC(=O)CBr$_3$, —NHC(=S)CBr$_3$, —NHC(=S)NH$_2$, —NHC(=O)NH$_2$, —NHC(=O)NHCH$_3$, —NHC(=S)NHCH$_3$, —NHC(=O)NHC$_2$H$_5$, —NHC(=S)NHC$_2$H$_5$, —NHC(=O)NH-nC$_3$H$_7$, —NHC(=S)NH-nC$_3$H$_7$, —NHC(=O)NH-iC$_3$H$_7$, —NHC(=S)NH-iC$_3$H$_7$, NHC(=S)NH-cyclopropyl, —NHC(=O)NH-cyclopropyl, NHC(=S)NH-cyclobutyl, —NHC(=O)NH-cyclobutyl, NHC(=S)NH-cyclopentyl, —NHC(=O)NH-cyclopentyl, NHC(=S)NH-cyclohexyl, —NHC(=O)NH-cyclohexyl, NHC(=O)NHC(=O)CH$_3$, NHC(=S)NHC(=O)CH$_3$ NHC(=O)NHC(=O)C$_2$H$_5$, NHC(=O)NH-heteroaryl, —NCS, pyrrolyl, pyrazolyl, imidazolyl, 1,2,3-triazol-1-yl, 1,2,4-triazol-1-yl.

It was observed that compounds comprising a thio group as indicated above seem to present a better solubility and a greater ability to cross biological membranes.

Considering the asymmetric configuration of the carbon atom in position 5 of the ring A, all above identified compounds are optically active. Therefore, the present invention concerns: racemic mixtures of these compounds, mixtures enriched in either one of the enantiomers, and either one of the isolated enantiomers. For the scopes of the present invention it is understood as racemic mixture a 50%:50% mixture of the two R and S enantiomers. It is understood as mixture enriched in one of the enantiomers a mixture containing more than 50% of one enantiomer (either S or R), for example 55%, 60%, 65%, 70%, 75%, or more. As isolated enantiomer it is understood a pure enantiomer, i.e. 100% or a mixture highly enriched of that enantiomer, for example 98%, 95%, 93%, 90%, 88%, 85%, 80%.

A specific form of embodiment of the invention implies compounds consisting of the S enantiomer or compositions comprising the S enantiomer as either enriched mixture or pure enantiomer. A second specific form of embodiment of the invention comprises compounds consisting of the R/S racemic mixtures or compositions comprising the R/S racemic mixtures. A further form of specific embodiment, less preferred, implies mixture enriched in the R enantiomer.

Preferred compounds having general formula (I) are listed in Table 1 below.

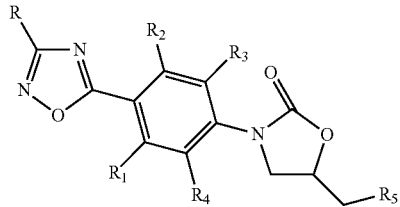

TABLE 1

| | R | R1 | R2 | R3 | R4 | R5 |
|---|---|---|---|---|---|---|
| 1 | Ph | H | H | H | H | NHC(=O)CH$_3$ |
| 2 | Ph | F | H | H | H | NHC(=O)CH$_3$ |
| 3 | Ph | F | F | H | H | NHC(=O)CH$_3$ |
| 4 | Ph | F | F | F | H | NHC(=O)CH$_3$ |
| 5 | Ph | F | F | F | H | NHC(=O)CH$_3$ |
| 6 | Ph | Cl | H | H | H | NHC(=O)CH$_3$ |
| 7 | Ph | Cl | Cl | H | H | NHC(=O)CH$_3$ |
| 8 | Ph | H | H | H | H | NHC(=S)CH$_3$ |
| 9 | Ph | F | H | H | H | NHC(=S)CH$_3$ |
| 10 | Ph | F | F | H | H | NHC(=S)CH$_3$ |
| 11 | Ph | Cl | H | H | H | NHC(=S)CH$_3$ |
| 12 | Ph | Cl | Cl | H | H | NHC(=S)CH$_3$ |
| 13 | Ph | F | F | F | H | NHC(=S)CH$_3$ |
| 14 | Ph | Br | H | H | H | NHC(=S)CH$_3$ |
| 15 (A3a) | CH$_3$ | H | H | H | H | NHC(=O)CH$_3$ |
| 16 (A3b) | CH$_3$ | F | H | H | H | NHC(=O)CH$_3$ |
| 17 | CH$_3$ | F | F | H | H | NHC(=O)CH$_3$ |
| 18 | CH$_3$ | F | F | F | H | NHC(=O)CH$_3$ |
| 19 | CH$_3$ | Cl | H | H | H | NHC(=O)CH$_3$ |
| 20 | CH$_3$ | Cl | Cl | H | H | NHC(=O)CH$_3$ |
| 21 | CH$_3$ | Br | H | H | H | NHC(=O)CH$_3$ |
| 22 (A4a) | CH$_3$ | H | H | H | H | NHC(=S)CH$_3$ |
| 23 (A4b) | CH$_3$ | F | H | H | H | NHC(=S)CH$_3$ |
| 24 | CH$_3$ | F | F | H | H | NHC(=S)CH$_3$ |
| 25 | CH$_3$ | Cl | H | H | H | NHC(=S)CH$_3$ |
| 26 | CH$_3$ | Cl | Cl | H | H | NHC(=S)CH$_3$ |
| 27 | CH$_3$ | F | F | F | H | NHC(=S)CH$_3$ |
| 28 | CH$_3$ | Br | H | H | H | NHC(=S)CH$_3$ |
| 29 | C$_2$H$_5$ | H | H | H | H | NHC(=O)CH$_3$ |
| 30 | C$_2$H$_5$ | F | H | H | H | NHC(=O)CH$_3$ |
| 31 | C$_2$H$_5$ | F | F | H | H | NHC(=O)CH$_3$ |
| 32 | C$_2$H$_5$ | F | F | F | H | NHC(=O)CH$_3$ |
| 33 | C$_2$H$_5$ | Cl | H | H | H | NHC(=O)CH$_3$ |
| 34 | C$_2$H$_5$ | Cl | Cl | H | H | NHC(=O)CH$_3$ |
| 35 | C$_2$H$_5$ | Br | H | H | H | NHC(=O)CH$_3$ |
| 36 | C$_2$H$_5$ | H | H | H | H | NHC(=S)CH$_3$ |
| 37 | C$_2$H$_5$ | F | H | H | H | NHC(=S)CH$_3$ |
| 38 | C$_2$H$_5$ | F | F | H | H | NHC(=S)CH$_3$ |
| 39 | C$_2$H$_5$ | Cl | H | H | H | NHC(=S)CH$_3$ |
| 40 | C$_2$H$_5$ | Cl | Cl | H | H | NHC(=S)CH$_3$ |
| 41 | C$_2$H$_5$ | F | F | F | H | NHC(=S)CH$_3$ |
| 42 | C$_2$H$_5$ | Br | H | H | H | NHC(=S)CH$_3$ |
| 43 | Ph | H | H | H | H | NHC(=O)NH$_2$ |
| 44 | Ph | F | H | H | H | NHC(=O)NH$_2$ |
| 45 | Ph | F | F | H | H | NHC(=O)NH$_2$ |
| 46 | Ph | F | F | F | H | NHC(=O)NH$_2$ |
| 47 | Ph | Br | H | H | H | NHC(=O)NH$_2$ |
| 48 | Ph | Cl | H | H | H | NHC(=O)NH$_2$ |
| 49 | Ph | Cl | Cl | H | H | NHC(=O)NH$_2$ |
| 50 | Ph | H | H | H | H | NHC(=S)NH$_2$ |
| 51 | Ph | F | H | H | H | NHC(=S)NH$_2$ |
| 52 | Ph | F | F | H | H | NHC(=S)NH$_2$ |
| 53 | Ph | Cl | H | H | H | NHC(=S)NH$_2$ |
| 54 | Ph | Cl | Cl | H | H | NHC(=S)NH$_2$ |
| 55 | Ph | F | F | F | H | NHC(=S)NH$_2$ |
| 56 | Ph | Br | H | H | H | NHC(=S)NH$_2$ |
| 57 | CH$_3$ | H | H | H | H | NHC(=O)NH$_2$ |
| 58 | CH$_3$ | F | H | H | H | NHC(=O)NH$_2$ |
| 59 | CH$_3$ | F | F | H | H | NHC(=O)NH$_2$ |
| 60 | CH$_3$ | F | F | F | H | NHC(=O)NH$_2$ |

TABLE 1-continued

| | R | R1 | R2 | R3 | R4 | R5 |
|---|---|---|---|---|---|---|
| 61 | $CH_3$ | Cl | H | H | H | $NHC(=O)NH_2$ |
| 62 | $CH_3$ | Cl | Cl | H | H | $NHC(=O)NH_2$ |
| 63 | $CH_3$ | Br | H | H | H | $NHC(=O)NH_2$ |
| 64 (B3a) | $CH_3$ | H | H | H | H | $NHC(=S)NH_2$ |
| 65 (B3b) | $CH_3$ | F | H | H | H | $NHC(=S)NH_2$ |
| 66 | $CH_3$ | F | F | H | H | $NHC(=S)NH_2$ |
| 67 | $CH_3$ | Cl | H | H | H | $NHC(=S)NH_2$ |
| 68 | $CH_3$ | Cl | Cl | H | H | $NHC(=S)NH_2$ |
| 69 | $CH_3$ | F | F | F | H | $NHC(=S)NH_2$ |
| 70 | $CH_3$ | Br | H | H | H | $NHC(=S)NH_2$ |
| 71 | $C_2H_5$ | H | H | H | H | $NHC(=O)NH_2$ |
| 72 | $C_2H_5$ | F | H | H | H | $NHC(=O)NH_2$ |
| 73 | $C_2H_5$ | F | F | H | H | $NHC(=O)NH_2$ |
| 74 | $C_2H_5$ | F | F | F | H | $NHC(=O)NH_2$ |
| 75 | $C_2H_5$ | Cl | H | H | H | $NHC(=O)NH_2$ |
| 76 | $C_2H_5$ | Cl | Cl | H | H | $NHC(=O)NH_2$ |
| 77 | $C_2H_5$ | Br | H | H | H | $NHC(=O)NH_2$ |
| 78 | $C_2H_5$ | H | H | H | H | $NHC(=S)NH_2$ |
| 79 | $C_2H_5$ | F | H | H | H | $NHC(=S)NH_2$ |
| 80 | $C_2H_5$ | F | F | H | H | $NHC(=S)NH_2$ |
| 81 | $C_2H_5$ | Cl | H | H | H | $NHC(=S)NH_2$ |
| 82 | $C_2H_5$ | Cl | Cl | H | H | $NHC(=S)NH_2$ |
| 83 | $C_2H_5$ | F | F | F | H | $NHC(=S)NH_2$ |
| 84 | $C_2H_5$ | Br | H | H | H | $NHC(=S)NH_2$ |
| 85 | Ph | H | H | H | H | $NHC(=O)NHCH_3$ |
| 86 | Ph | F | H | H | H | $NHC(=O)NHCH_3$ |
| 87 | Ph | F | F | H | H | $NHC(=O)NHCH_3$ |
| 88 | Ph | F | F | F | H | $NHC(=O)NHCH_3$ |
| 89 | Ph | Br | H | H | H | $NHC(=O)NHCH_3$ |
| 90 | Ph | Cl | H | H | H | $NHC(=O)NHCH_3$ |
| 91 | Ph | Cl | Cl | H | H | $NHC(=O)NHCH_3$ |
| 92 | Ph | H | H | H | H | $NHC(=S)NHCH_3$ |
| 93 | Ph | F | H | H | H | $NHC(=S)NHCH_3$ |
| 94 | Ph | F | F | H | H | $NHC(=S)NHCH_3$ |
| 95 | Ph | Cl | H | H | H | $NHC(=S)NHCH_3$ |
| 96 | Ph | Cl | Cl | H | H | $NHC(=S)NHCH_3$ |
| 97 | Ph | F | F | F | H | $NHC(=S)NHCH_3$ |
| 98 | Ph | Br | H | H | H | $NHC(=S)NHCH_3$ |
| 99 | $CH_3$ | H | H | H | H | $NHC(=O)NHCH_3$ |
| 100 | $CH_3$ | F | H | H | H | $NHC(=O)NHCH_3$ |
| 101 | $CH_3$ | F | F | H | H | $NHC(=O)NHCH_3$ |
| 102 | $CH_3$ | F | F | F | H | $NHC(=O)NHCH_3$ |
| 103 | $CH_3$ | Cl | H | H | H | $NHC(=O)NHCH_3$ |
| 104 | $CH_3$ | Cl | Cl | H | H | $NHC(=O)NHCH_3$ |
| 105 | $CH_3$ | Br | H | H | H | $NHC(=O)NHCH_3$ |
| 106 (B4a) | $CH_3$ | H | H | H | H | $NHC(=S)NHCH_3$ |
| 107 (B4b) | $CH_3$ | F | H | H | H | $NHC(=S)NHCH_3$ |
| 108 | $CH_3$ | F | F | H | H | $NHC(=S)NHCH_3$ |
| 109 | $CH_3$ | Cl | H | H | H | $NHC(=S)NHCH_3$ |
| 110 | $CH_3$ | Cl | Cl | H | H | $NHC(=S)NHCH_3$ |
| 111 | $CH_3$ | F | F | F | H | $NHC(=S)NHCH_3$ |
| 112 | $CH_3$ | Br | H | H | H | $NHC(=S)NHCH_3$ |
| 113 | $C_2H_5$ | H | H | H | H | $NHC(=O)NHCH_3$ |
| 114 | $C_2H_5$ | F | H | H | H | $NHC(=O)NHCH_3$ |
| 115 | $C_2H_5$ | F | F | H | H | $NHC(=O)NHCH_3$ |
| 116 | $C_2H_5$ | F | F | F | H | $NHC(=O)NHCH_3$ |
| 117 | $C_2H_5$ | Cl | H | H | H | $NHC(=O)NHCH_3$ |
| 118 | $C_2H_5$ | Cl | Cl | H | H | $NHC(=O)NHCH_3$ |
| 119 | $C_2H_5$ | Br | H | H | H | $NHC(=O)NHCH_3$ |
| 120 | $C_2H_5$ | H | H | H | H | $NHC(=S)NHCH_3$ |
| 121 | $C_2H_5$ | F | H | H | H | $NHC(=S)NHCH_3$ |
| 122 | $C_2H_5$ | F | F | H | H | $NHC(=S)NHCH_3$ |
| 123 | $C_2H_5$ | Cl | H | H | H | $NHC(=S)NHCH_3$ |
| 124 | $C_2H_5$ | Cl | Cl | H | H | $NHC(=S)NHCH_3$ |
| 125 | $C_2H_5$ | F | F | F | H | $NHC(=S)NHCH_3$ |
| 126 | $C_2H_5$ | Br | H | H | H | $NHC(=S)NHCH_3$ |
| 127 (B2a) | $CH_3$ | H | H | H | H | NCS |
| 128 (B2b) | $CH_3$ | F | H | H | H | NCS |
| 129 | $CH_3$ | F | F | H | H | NCS |
| 130 | $CH_3$ | Cl | H | H | H | NCS |
| 131 | $CH_3$ | Cl | Cl | H | H | NCS |
| 132 | $CH_3$ | F | F | F | H | NCS |
| 133 | $CH_3$ | Br | H | H | H | NCS |
| 134 | $CH_3$ | H | H | H | H | $NHC(=O)NHC(=O)CH_3$ |
| 135 | $CH_3$ | F | H | H | H | $NHC(=O)NHC(=O)CH_3$ |
| 136 | $CH_3$ | F | F | H | H | $NHC(=O)NHC(=O)CH_3$ |
| 137 | $CH_3$ | Cl | H | H | H | $NHC(=O)NHC(=O)CH_3$ |
| 138 | $CH_3$ | Cl | Cl | H | H | $NHC(=O)NHC(=O)CH_3$ |
| 139 | $CH_3$ | F | F | F | H | $NHC(=O)NHC(=O)CH_3$ |
| 140 | $CH_3$ | Br | H | H | H | $NHC(=O)NHC(=O)CH_3$ |
| 141 | $CH_3$ | H | H | H | H | $NHC(=S)NHC(=O)CH_3$ |
| 142 | $CH_3$ | F | H | H | H | $NHC(=S)NHC(=O)CH_3$ |
| 143 | $CH_3$ | F | F | H | H | $NHC(=S)NHC(=O)CH_3$ |
| 144 | $CH_3$ | Cl | H | H | H | $NHC(=S)NHC(=O)CH_3$ |
| 145 | $CH_3$ | Cl | Cl | H | H | $NHC(=S)NHC(=O)CH_3$ |
| 146 | $CH_3$ | F | F | F | H | $NHC(=S)NHC(=O)CH_3$ |
| 147 | $CH_3$ | Br | H | H | H | $NHC(=S)NHC(=O)CH_3$ |
| 148 (A1a) | $CH_3$ | H | H | H | H | I |
| 149 (A1b) | $CH_3$ | F | H | H | H | I |
| 150 | $CH_3$ | F | F | H | H | I |
| 151 | $CH_3$ | Cl | H | H | H | I |
| 152 | $CH_3$ | Cl | Cl | H | H | I |
| 153 | $CH_3$ | F | F | F | H | I |
| 154 | $CH_3$ | Br | H | H | H | I |
| 155 (B1a) | $CH_3$ | H | H | H | H | 1,2,3-triazol-1-yl |
| 156 (B1b) | $CH_3$ | F | H | H | H | 1,2,3-triazol-1-yl |
| 157 | $CH_3$ | F | F | H | H | 1,2,3-triazol-1-yl |
| 158 | $CH_3$ | Cl | H | H | H | 1,2,3-triazol-1-yl |
| 159 | CH3 | Cl | Cl | H | H | 1,2,3-triazol-1-yl |
| 160 | CH3 | F | F | F | H | 1,2,3-triazol-1-yl |
| 161 | CH3 | Br | H | H | H | 1,2,3-triazol-1-yl |

Each compound identified above is intended as the S enantiomer as well as a mixture enriched with the S enantiomer or a racemic mixture. For compounds 127-133 and 148-161 is understood as the R-enantiomer is preferred as pure as a mixture enriched in R-enantiomer.

Preparation of Invented Compounds

The synthesis of compounds of interest A and B and of the corresponding intermediates, is described below. The invented compounds were synthesized starting from the construction of the 1,2,4-oxadiazole ring by following the classic amidoxime route (Scheme 1) as reported in [9]. Thus, amidoxime 1 was reacted with the corresponding benzoyl chloride 2, producing 1,2,4-oxadiazoles 3. The latter compounds, where the para position is activated to undergo an Aromatic Nucleophilic Substitution, [10-13] were with allylamine, yielding compounds 4. Reaction with di-(t-butyl)-dicarbonate and subsequent cyclization [14] of the resulting derivatives 5, yielded oxazolidinones of interest A1 as ideal precursors for further side-chain modifications.

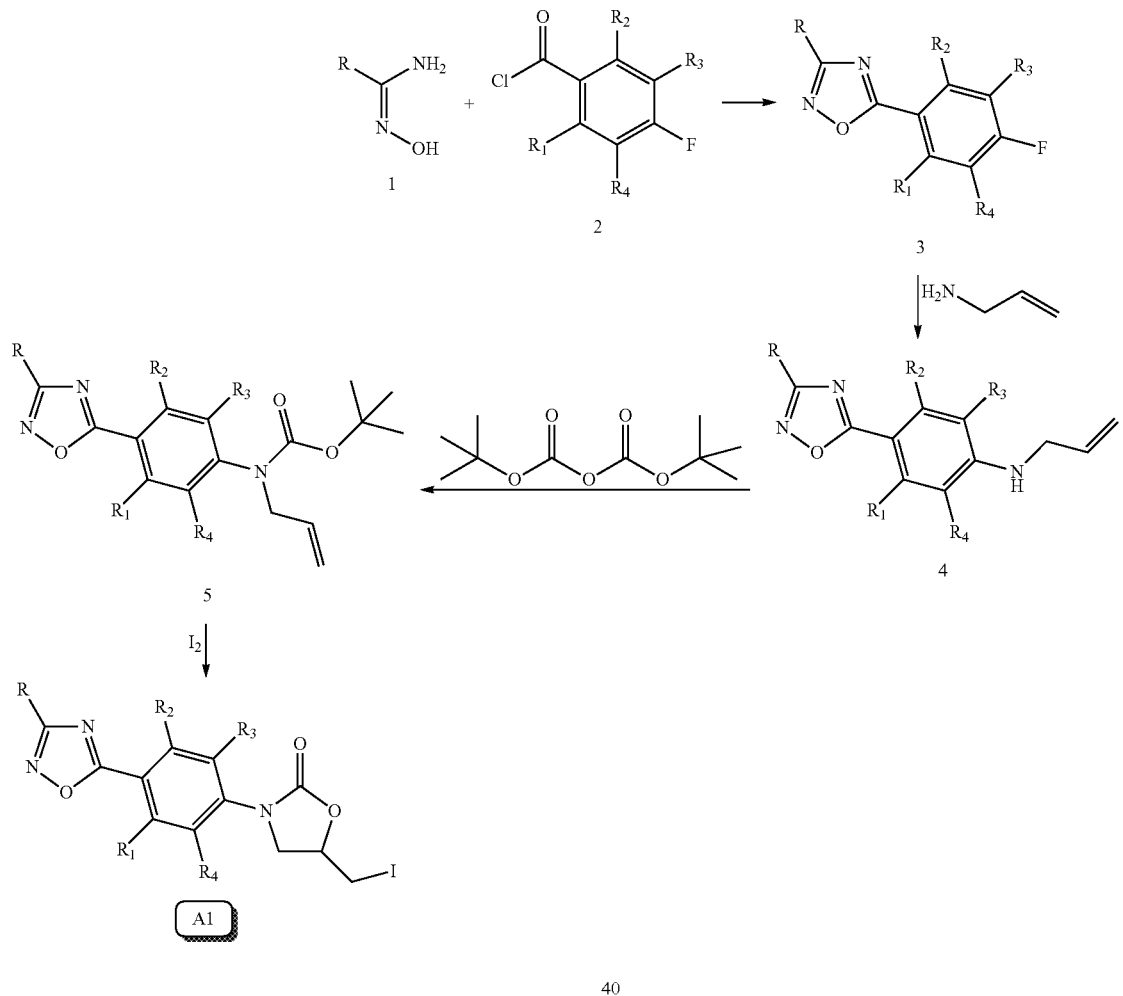

The subsequent functionalization of the side-chain (Scheme 2) included the acetamidomethyl moiety A3, as well as the corresponding thioamides A4, thioureas B4 and azolic derivatives A5-7, B1.

The azide precursors A2 were obtained by reaction of compounds A1 with an azide source. Their subsequent reduction yielded the corresponding amino derivatives 6 [15]. The amino derivatives 6 were readily reacted with acetyl chloride or acetic anhydride, giving compounds A3. The acetamidomethyl derivatives A3, were reacted with sulfurating reagents (i.e. Lawesson's Reagent or $P_2S_5$) yielding thioamide derivatives A4 (Scheme 2).

The azole derivatives A5-7, B1, were obtained by means of nucleophilic substitution starting from iodo-derivatives A1, while (thio)ureas B4 were obtained through reactions of amines 6 with iso(thio)cyanates (Scheme 2).

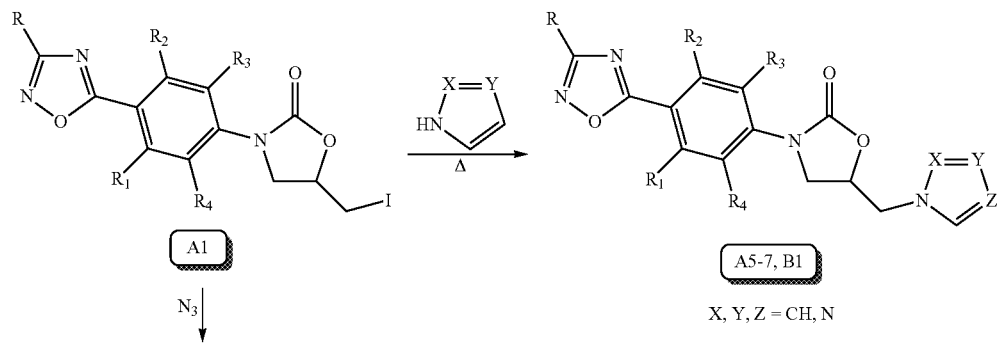

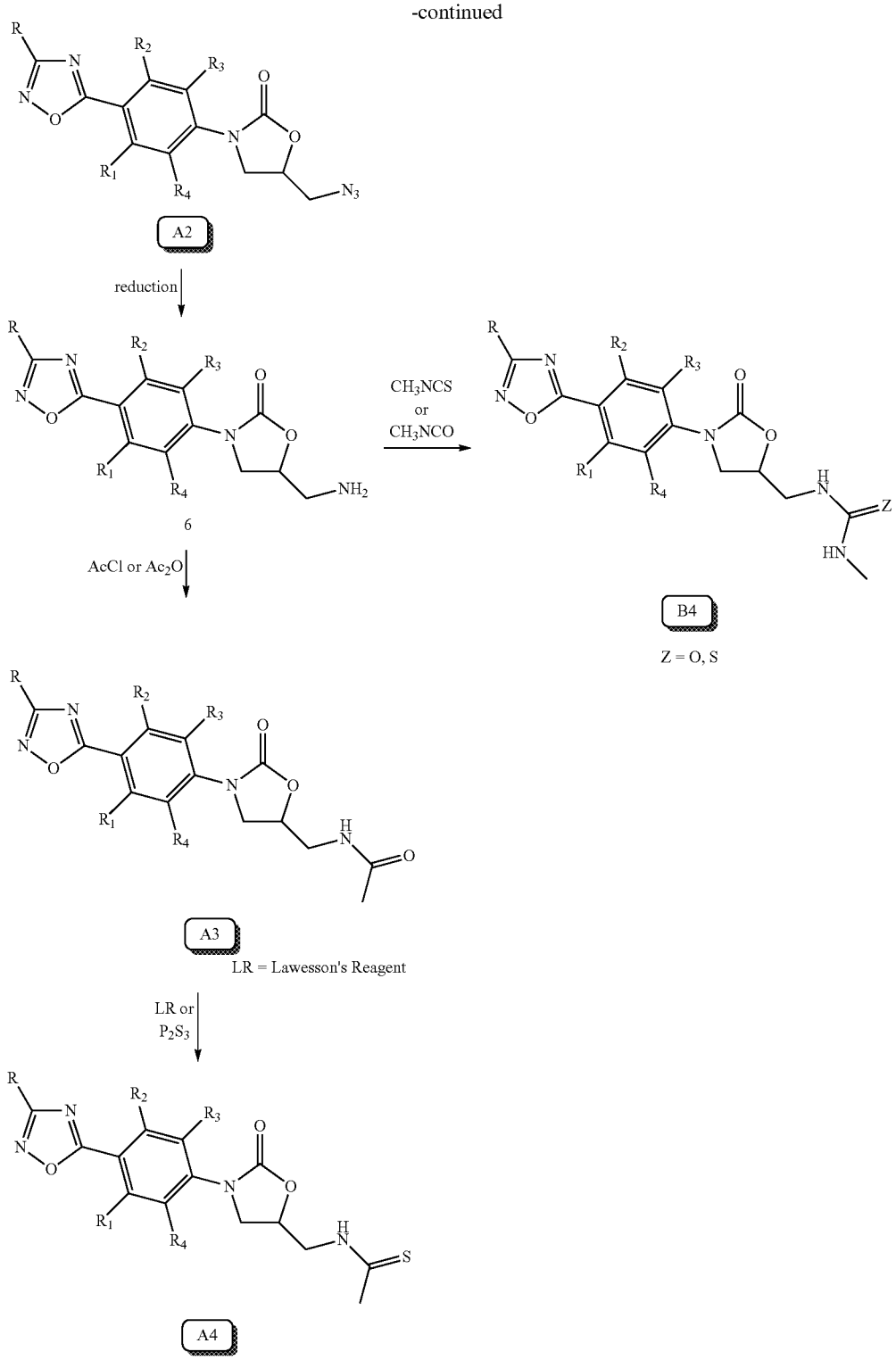

The so obtained compounds, synthesized as racemic mixtures, were resolved into the corresponding enantiomers (S or R) through HPLC separations by using a chiral stationary phase.

The Pharmaceutical Compositions

Pharmaceutical compositions suitable for administration of the compounds of the invention are compositions designed for oral, parenteral or topical usage.

Oral compositions may be, for example, in the form of tablet, coated tablet, hard capsule, soft capsule, syrup, solution, suspension, emulsion. Parenteral compositions may be, for example, in the form of aqueous or oily solution or emulsion. Topical compositions may be for example in the form of ointment, cream, gel, solution, O/W or W/O emulsion, or suspension.

In a specific embodiment the compositions are administered via inhalation.

In the preparation of pharmaceutical compositions one or more compounds of the invention are mixed with various therapeutically acceptable excipients suitable for solid, liquid or pasty compositions.

The suspensions/emulsions, whatever were their route of administration, may comprise nanoparticles and/or liposomes as a vehicle or carrier of the medicament.

Since some persistent lung infections often show a low rate of response to conventional therapy, in part due to the lack of selectivity of the drugs, in part to their low bioavailability, especially when administered systemically, particular attention has been given, within of the present invention, to the route of administration by endotracheal inhalation as an alternative to non-invasive systemic delivery of the compounds described herein.

Therefore, a specific embodiment of the invention involves the administration by endotracheal inhalation of the drug, preferably encapsulated in nanoparticles.

In fact, the nano-encapsulation of drugs and their pulmonary release promote a higher accumulation and retention of the drug within the lungs. The main advantage of this formulation and the route of administration is to be able to treat topically compartmentalized diseases such as those within the lung or bronchus, allowing the administration of high doses of the drug involved in the district and with reduced systemic toxicity, and therefore a reduced probability of giving rise to systemic side effects;

Formulations based on nanoparticle-carrier offer the additional advantage of improving the crossing of biological membranes such as the outer membrane of the bacteria, expanding the spectrum of action of drugs active also against Gram-negative bacteria;

In particular, we have developed solid lipid nanoparticles nebulizer-compatible (Nebulizer-Compatible Solid Lipid Nanoparticle (SLN)s) for the release of antimicrobial agents of the invention. SLN can be used as a vehicle for the pulmonary or bronchial release of antimicrobial drugs, improving stability as well as the in vivo retention time in the lungs, thus obtaining an increased bioavailability.

The studies on the pharmacokinetics and biodistribution of SLN have shown that interstitial lung macrophages, in more close contact with the circulation compared to alveolar macrophages, significantly contribute to the SLN uptake. Moreover, it was seen that factors such as prolonged circulation time, lower exposure of drugs at the renal level and markedly increased deposit in lung tissues are important characteristics for antimicrobial compounds also effective in the treatment of pneumonia caused by beta-lactams resistant bacteria (eg. methicillin-resistant *Staphylococcus aureus* (MRSA)).

Therapeutic Applications

The claimed compounds are new antibiotics intended for use in the treatment of infections caused by bacteria, essentially extremely resistant by Gram-positive bacteria. For example, but not limited to, *Staphylococcus* spp, *Enterococcus* spp, *Streptococcus* spp, in particular in the treatment of infections caused by *Staphylococcus* aureus, *Staphylococcus epidermidis*, *Enterococcus faecium*, *Enterococcus faecalis*, *Streptococcus pneumoniae*, *Haemophilus influenzae*, *Haemophilus parainfluenzae*, *Moraxella catarrhalis*. The compounds of the invention have proved to be active also on bacteria resistant to other antibiotics or resistant to the reference compound, linezolid. Advantageously, the compounds of the invention are effective even against bacteria resistant to more than one antibiotic, against multi-resistant bacteria, for example to two or more antibiotics selected from methicillin, vancomycin, penicillin, macrolides, fluoroquinolones or linezolid.

Furthermore, the novel compounds of the invention combine the inhibitory or bactericidal activity against both susceptible or (multi)resistant bacteria to known antibiotics to an entirely acceptable toxicity or even less than that of the reference compound, linezolid, thus offering an entirely beneficial clinical/therapeutic profile.

Without linking the invention to some particular scientific theories, the effectiveness of the compounds of the invention in the treatment of bacterial infections, especially those caused by bacteria also resistant to other antibiotics, seems to be based on mechanisms of action involving modulation and/or inhibition of bacterial protein synthesis and/or activity. The effectiveness of the molecules of the invention seems to be linked, in theory, not only to an interaction with proteins responsible for the resistance mechanisms developed by bacteria, such as for example, the protein expressed by PBP2a MRSA strains (*Staphylococcus aureus* metacillina-resistant), but also to an interaction of the compounds of the invention with mechanisms of ribosomal protein synthesis.

EXPERIMENTAL SECTION

Evaluation of the Pharmacological Activity
Microbiological Assays
(i) Bacterial Strains Several well characterized for their antibiotic-susceptibility phenotype *Staphylococcus aureus* isolates were used for the determination of the in vitro antibacterial activity of the studied compounds. In particular, *S. aureus* ATCC 29213 reference standard strain and *S. aureus* M923 (collection strain) were used as MSSA strains. Among MRSA, *S. aureus* MU50 (ATCC 700699) reference standard strain and two collection strains (433 and F511) were used for susceptibility assays.

In particular, eleven linezolid-resistant coagulase-negative staphylococci (CoNS) (ten *S. epidermidis* and one *S. hominis*) were investigated. The eleven linezolid-resistant strains were isolated in several hospital settings between 2010 and 2011 from positive blood cultures. For the comparison of the antimicrobial activities of the different compounds a collection of forty linezolid-susceptible MRSA, recently isolated from patients with cystic fibrosis, showing different profiles of multi-resistance to different classes of antimicrobials, was used (Table 4 and 5).

(ii) Determination of Minimum Inhibitory Concentrations (MICs)

The in vitro antibacterial activity of the new agents was studied by determining their minimum inhibitory concentrations (MICs) by means of the broth microdilution method according to the Clinical and Laboratory Standards Institute (CLSI) guidelines.[16] Briefly, serial 2-fold dilutions of each compound were made using the Cation adjusted Mueller-Hinton broth (CAMHB) in microtitre plates with 96 wells. Dimethyl sulfoxide (DMSO) was used as solvent for all the synthesized compounds. An equal volume of the bacterial inoculum ($1 \times 10^6$ CFU/mL) was added to each well on the microtitre plate containing 0.05 mL of the serial antibiotic dilutions. The microtitre plate was then incubated at 37° C. for 18-24 h after which each well was analysed for the presence of bacterial growth. The MIC was defined as the lowest concentration of antimicrobial agent able to cause inhibition of bacterial growth as shown by the lack of turbidity of the culture medium. The in vitro antibacterial activities of new linezolid-like 1,2,4-oxadiazoles were tested and compared to that of reference oxazolidinone in clinical use: Linezolid (Sigma-Aldrich). Final DMSO concentrations were also taken into account in all the biological assays.

Minimum Inhibitory Concentration Test

Fourteen new compounds in racemic mixture (group A), as following shown, were analyzed for their antibacterial activity against strains of *Staphylococcus aureas* in terms of reference standard strains and clinical strains, both methicillin-susceptible (MSSA) or methicillin-resistant (MRSA).

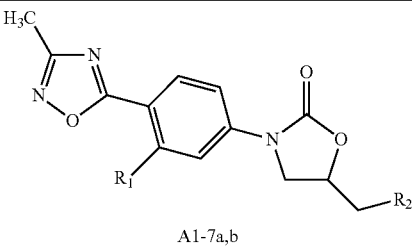

A1-7a,b

|     | R$_1$ | R$_2$ |
| --- | --- | --- |
| A1a | H | I |
| A1b | F | I |
| A2a | H | N$_3$ |
| A2b | F | N$_3$ |
| A3a | H | NH(C=O)CH$_3$ |
| A3b | F | NH(C=O)CH$_3$ |
| A4a | H | NH(C=S)CH$_3$ |
| A4b | F | NH(C=S)CH$_3$ |
| A5a | H | pyrazol-1-yl |
| A5b | F | pyrazol-1-yl |
| A6a | H | imidazol-1-yl |
| A6b | F | imidazol-1-yl |
| A7a | H | 1,2,4-triazol-1-yl |
| A7b | F | 1,2,4-triazol-1-yl |

The antimicrobial activities, summarized in Table 2, were determined by the "gold standard" method of broth microdilution, as recommended by the Clinical Laboratory Standards Institute (CLSI) (See the Experimental Section). The minimum inhibitory concentrations (MIC) values were expressed in µg/mL, and cell viability tests were performed to evaluate the antibacterial selective toxicity of most active compounds. Linezolid has been used as a reference antibiotic. In detail, the bacterial strains were tested: *Staphylococcus aureus* ATCC 29213, a clinical strain of methicillin-susceptible *S. aureus* (M923), *S. aureus* MU50 (methicillin-resistant—MRSA), and two methicillin-resistant clinical strains, 433 and F511. All strains tested were found to be linezolid-susceptible. Among these molecules the most active, in racemic form, have proved to be A4a and A4b compounds.

TABLE 2

| | MIC (µg/mL) | | | | |
| --- | --- | --- | --- | --- | --- |
| Comp. A | ATCC 29213 | MSSA M923 | MRSA MU50 | MRSA 433 | MRSA F511 |
| A1a | >50 | >50 | 50 | 25 | 50 |
| A1b | >50 | >50 | 50 | 50 | >50 |
| A2a | >50 | >50 | >50 | >50 | >50 |
| A2b | >50 | >50 | >50 | >50 | >50 |
| A3a | 12.5 | 6.25 | 6.25 | 1.6 | 12.5 |
| A3b | 12.5 | 6.25 | 6.25 | 1.6 | 12.5 |
| A4a | 3.13 | 1.6 | ≤0.4 | 1.6 | 1.6 |
| A4b | 1.6 | 1.6 | ≤0.4 | 0.8 | 1.6 |
| A5a | >50 | >50 | >50 | >50 | >50 |
| A5b | >50 | >50 | >50 | >50 | >50 |
| A6a | >50 | >50 | >50 | >50 | >50 |
| A6b | >50 | >50 | >50 | >50 | >50 |
| A7a | >50 | >50 | >50 | >50 | >50 |
| A7b | >50 | >50 | >50 | >50 | >50 |
| Linezolid | ≤0.4 | 3.13 | 0.8 | 1.6 | 3.13 |

Compounds A3a, A3b, A4a, A4b, A1a, A1b correspond to the compounds 15, 16, 22, 23, 148 and 149 of Table 1

Four of the fourteen tested compounds (see Table 2) showed MIC values, both against MSSA and MRSA strains, with potency comparable or superior to that of linezolid. Furthermore, a better activity against MSSA and MRSA strains compared to linezolid has been displayed by derivatives containing sulfur A4a and A4b, while compounds A3a, and A3b were shown to be less active than linezolid, except for the MRSA strain 433. The comparison with the linezolid should take account of the fact that the tested compounds were used as a racemic mixture, then the antibacterial activity of A3a, A3b, A4a and A4b is presumed to be underestimated compared to the pure more active enantiomer.

Of other compounds (group B), shown below, were assessed the activities of both the racemic mixture and S and R enantiomers.

B1-4a,b

|     | R$_1$ | R$_2$ |
| --- | --- | --- |
| B1a | H | 1,2,3-triazol-1-yl |
| B1b | F | 1,2,3-triazol-1-yl |
| B2a | H | NCS |
| B2b | F | NCS |
| B3a | H | NH(C=S)NH$_2$ |
| B3b | F | NH(C=S)NH$_2$ |
| B4a | H | NH(C=S)NHCH$_3$ |
| B4b | F | NH(C=S)NHCH$_3$ |

The antimicrobial activities, summarized in Table 3, were determined by the "gold standard" method of broth microdilution, as recommended by the Clinical Laboratory Standards Institute (CLSI) (See the Experimental Section). The minimum inhibitory concentration (MIC) values were expressed in µg/mL. Linezolid has been used as a reference antibiotic. In detail, the tested bacterial strains were: *Staphylococcus aureus* ATCC 29213, a clinical strain of methicillin-susceptible *S. aureus* (M923), *S. aureus* MU50 (methicillin-resistant—MRSA) strain, and two methicillin-resistant clinical strains, 433 and F511. All strains tested were found to be linezolid-susceptible. Among tested new molecules the most active, in racemic form, have proved to be B4a and B4b compounds, followed by B1a and B1b possessing a fair amount of activity (Table 3).

TABLE 3

| | MIC (µg/mL) | | | | |
| --- | --- | --- | --- | --- | --- |
| Comp. B | ATCC 29213 | MSSA M923 | MRSA MU50 | MRSA 433 | MRSA F511 |
| B1a | 25 | 25 | 3.125 | 12.5 | 12.5 |
| B1b | 25 | 25 | 1.6 | 6.25 | 12.5 |
| B2a | >50 | >50 | >50 | >50 | 50 |
| B2b | >50 | >50 | >50 | >50 | >50 |
| B3a | >50 | >50 | >50 | >50 | >50 |
| B3b | >50 | >50 | >50 | >50 | >50 |
| B4a | 6.25 | 6.25 | 1.6 | 3.125 | 6.25 |
| B4b | 6.25 | 6.25 | 1.6 | 3.125 | 6.25 |
| Linezolid | ≤0.4 | 3.125 | 0.8 | 1.6 | 3.125 |

Among these, B4a and B4b compounds (corresponding to compounds 106 and 107 of Table 1) showed an antibacterial activity very similar to that of linezolid against linezolid-susceptible *S. aureus* strains.

In a completely surprising manner, the same compounds, resolved into their enantiomers, have demonstrated efficacy from 8 to 32 times higher than linezolid against linezolid-resistant *Staphylococcus* spp. strains. The results are reported in Tables 4 and 5. In one case (A4bS) it is quite completely reversed resistance to linezolid into susceptibility. Of these molecules enantiomeric separations have allowed to assign the power to the S enantiomer, while the R proved to be inactive (see Table 4).

The compounds B4a and B4b correspond to racemic mixtures of the two compounds B4a and B4b, the compounds B4bS and B4bR and B4aS and B4aR are resolved S and R enantiomers, respectively.

TABLE 4

MIC values
MIC-range ≤0.06 - >128 μg/ml

| Compound | 84b | 84bS | 84bR | 84a | 84aS | 84aR | LZD | DA |
|---|---|---|---|---|---|---|---|---|
| tested strains: 6 ATCC (4MSSA, 2 MRSA)plus45 MRSA all LZD sensitive | | | | | | | | |
| MIC-range | 0.5-16 | 0.5-8 | 64->128 | 1-16 | 0.5-8 | 128->128 | 0.25-16 | <0.06->128 |
| $MIC_{50}$ | 4 | 2 | >128 | 8 | 2 | >128 | 2 | <0.06 |
| $MIC_{90}$ | 16 | 4 | >128 | 16 | 4 | >128 | 4 | >128 |
| tested strains: 12 MRSE all LZD sensitive | | | | | | | | |
| MIC range | 32->126 | 8.16 | >126 | 32->126 | 8-32 | >128 | 32-64 | 0.12-1 |
| $MIC_{50}$ | 64 | 8 | >128 | 64 | 16 | >128 | 32 | 0.5 |
| $MIC_{90}$ | 128 | 8 | >128 | >128 | 32 | >128 | 64 | 1 |

TABLE 5

MIC-range 0.06-128 g/mL

| Strains | A4aS | A4aR | A4bS | A4bR | LZD |
|---|---|---|---|---|---|
| ATCC *S. aureus* 29213 | 8 | 128 | 4 | 64 | 4 |
| ATCC *E. faecalis* 29212 | 4 | >128 | 2 | 32 | 1 |
| 11 Linezolid-resistant CoNS | | | | | |
| *S. epidermidis* Strain 1 | 8 | >128 | 8 | 128 | 64 |
| *S. epidermidis* Strain 2 | 32 | >128 | 8 | >128 | 64 |
| *S. epidermidis* Strain 3 | 4 | >128 | 4 | >128 | 64 |
| *S. epidermidis* Strain 4 | 32 | >128 | 4 | 128 | 64 |
| *S. epidermidis* Strain 5 | 4 | >128 | 2 | 128 | 64 |
| *S. epidermidis* Strain 6 | 4 | >128 | 4 | 64 | 32 |
| *S. epidermidis* Strain 7 | 32 | >128 | 8 | >128 | 32 |
| *S. epidermidis* Strain 8 | 32 | >128 | 2 | 128 | 32 |
| *S. epidermidis* Strain 9 | 1 | >128 | 1 | >128 | 32 |
| *S. epidermidis* Strain 10 | 8 | >128 | 4 | 128 | 32 |
| *S. hominis* Strain 11 | 8 | >128 | 4 | 128 | 32 |
| MIC-range | 1-32 | >128 | 1-8 | 64->128 | 32-64 |
| $MIC_{50}$ | 8 | >128 | 4 | 128 | 32 |
| $MIC_{90}$ | 32 | >128 | 8 | 128 | 64 |
| 45 Linezolid-susceptible MRSA | | | | | |
| $MIC_{50}$ | 2 | >128 | 0.5 | 128 | 2 |

Cell Viability (Cytotoxicity Assay)

To assess if the effect shown against bacterial cells could be related to a selected toxicity or to a more general toxic effect, we performed a first level assay in different types of eukaryotic cell lines to screen the new compounds for their general cytotoxic activity.

Cell Viability

The effects of A4b, (compound 23 of Table 1) and linezolid on cells viability were in vitro studied on PK15 (porcine kidney epithelial), HaCaT (human keratinocytes), and HepG2 (human hepatocellular carcinoma) cell lines. [17-19] HepG2 and HaCat cells were grown in Dulbecco's modified eagles medium (DMEM) whereas PK15 in DMEM/M199 (1:1). All media were supplemented with 10% heat inactivated foetal bovine serum (FBS), 2 mM L-glutamine, 100 units/mL penicillin and 100 μg/mL streptomycin. Cells were maintained at 37° C. in a 5% $CO_2$ atmosphere. All reagents for cell culture were from Euroclone (Pero, Italy).

Cell viability was measured by the MTT assay.[20] Briefly, MTT [3-(4,5-Dimethylthiazol-2-yl)-2,5-diphenyltetrazolium bromide] stock solution (5 mg/mL) was added to each well to a final concentration of 1.2 mM, and cells were incubated for 1 hour and 30 minutes at 37° C. After removing MTT solution, the reaction was stopped by adding 90% ethanol. Resuspended cells were centrifuged 10 min at 800×g. The absorbance was measured with the multilabel Victor[3] spectrophotometer (Perkin Elmer, Turku, Finland) at wavelength of 570 nm. Data are means±S.E. of 3 separate experiments performed in triplicate.

Statistical Analysis

Statistical significance was obtained with Student'st test in comparison with controls *=P≤0.05, **=P≤0.001. Data are means±S.E. of 3 separate experiments performed in triplicate.

All tested cell lines were treated with increasing concentrations (5-400 μg/mL) of A4a, and linezolid as reference compound. Another control was DMSO used as solvent.

Figure 2:
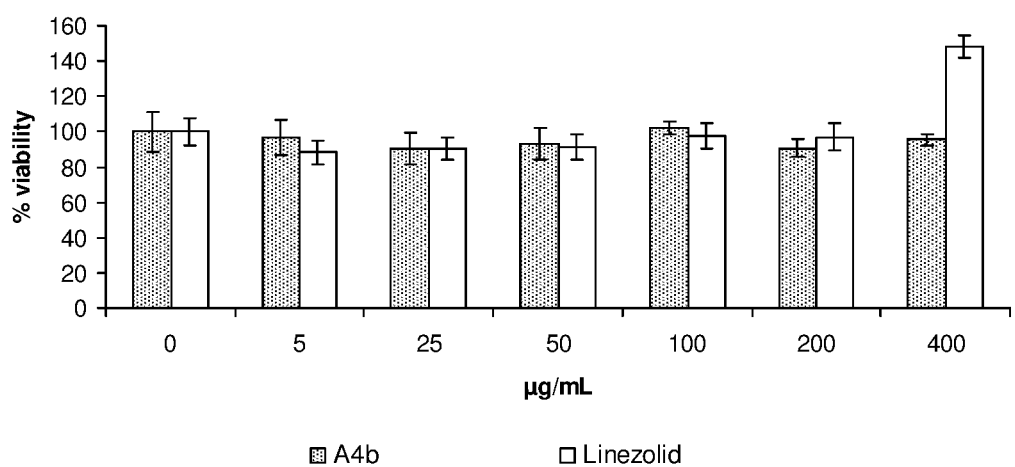
FIG. 2. Results of cell viability assays on PK15 cells treated with the A4b compound (compound 23 of table 1) and linezolid. Limits of significance: *=P<0.05, **=P<0.01.

The A4b molecule induced a moderate reduction of viability (less than 10%) in the PK15 cell line, with statistical significance at the concentrations of 25 (P<0.01), 50 (P<0.05) and 200 □g/mL (P<0.05), respectively (FIG. 2). This trend is comparable to that obtained with linezolid at the same concentrations.

Figure 3:
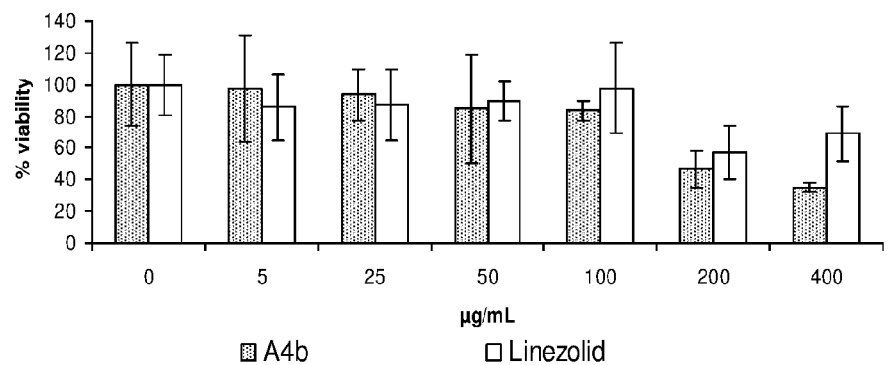
FIG. 3. Results of cell viability assays on HaCaT cells treated with the A4b compound (compound 23 of table 1) and linezolid. Limits of significance: *=P<0.05, **=P<0.01.

The reduction of cell viability caused by the A4b molecule was slightly more evident in the HaCaT cell line, reaching levels of statistically significant mortality compared to the values obtained with linezolid only at a concentration of 400 □g/mL (P<0.01; FIG. 3).

Figure 4:
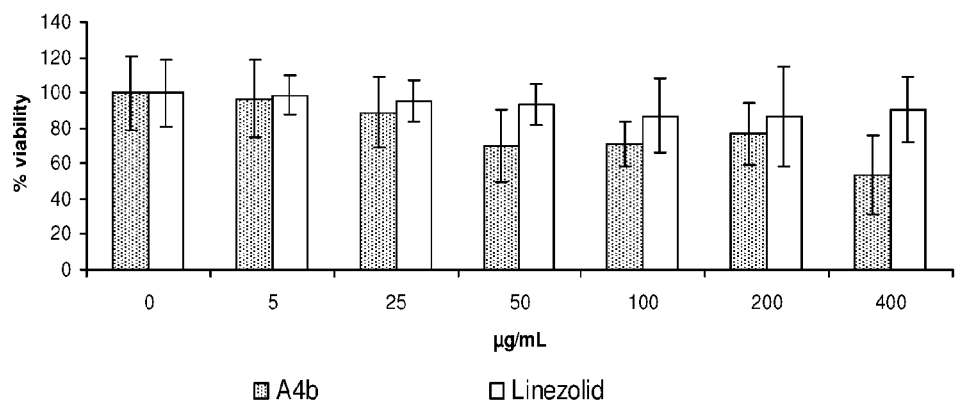
FIG. 4. Results of cell viability on HepG2 cells treated with the A4b compound (compound 23 of table 1) and linezolid. Limits of significance: *=P<0.05, **=P<0.01.

HepG2 cells showed a reduction in viability from 50 □g/mL of the A4b compound (FIG. 4).

They were then in vitro evaluated the effects of B4a and B4b molecules on cell viability on human hepatoma cell line, HepG2 and comparison with cytotoxicity induced by linezolid (negative control).

The cells are cultured in Dulbecco's modified eagles medium (DMEM) supplemented by 10% heat inactivated fetal bovine serum (FBS), L-glutamine at a final concentration of 2 mM, 100 units/mL of penicillin and 100 micrograms/mL of streptomycin. The cells were maintained at 37° C. in a 5% of $CO_2$ atmosphere.

Cytotoxic treatment: cells, plated at a density of 40,000 cell/cm[2] and maintained in culture for two days, were treated for 48 hours with increasing concentrations (25-100 □g/ml) of both enantiomers of B4a and B4b substances.

Cell viability was evaluated by an PrestoBlue® Cell Viability Reagent assay, a solution containing resazurin that permeates into cells and exploits the reducing power when they are alive and metabolically active. Briefly, the PrestoBlue® solution is administered directly to the medium of the cells in culture following the instructions of the manufacturer that has supplied the product. The cells are incubated for 1 hour at 37° C., at which time the PrestoBlue® solution, metabolized by living cells changes the staining from blue to red. The absorbance is measured using a Victor3 multifunction spectrophotometer (Perkin Elmer, Turku, Finland) at a wavelength of 570 nm. The obtained results and represented in the graph correspond to the mean±SE of independent experiments performed in triplicate.

The HepG2 cell line was subjected to treatment with increasing concentrations (25-100 µg/mL) of both enantiomers of the B4a and B4b molecules. Linezolid is used as a reference molecule only to a final concentration of 100 micrograms/mL. Moreover, as an additional control, cells are also treated with 0.9% DMSO, used as a solvent of the substances.

Figure 5:
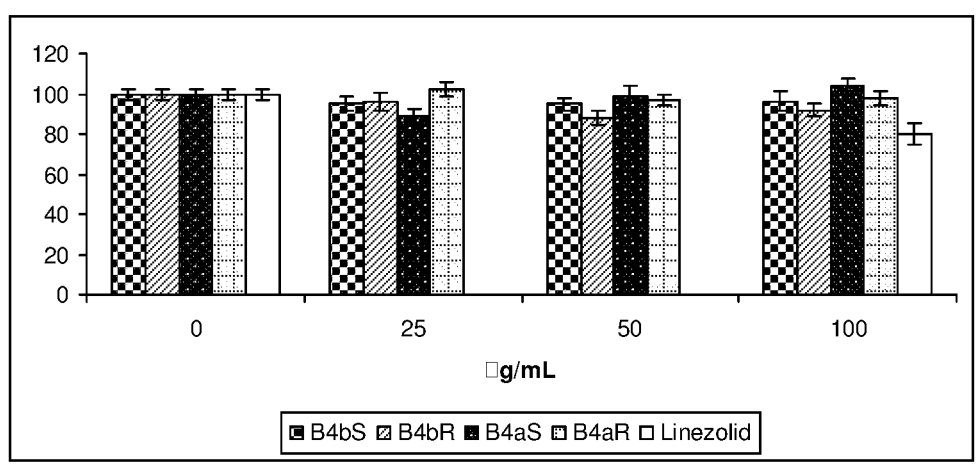
FIG. 5. Results of cell viability on HepG2 cells treated with B4a and B4b compounds (compounds 106 and 107 of Table 1) in the form of their respective enantiomers.

Both enantiomers of the B4b molecule have induced a moderate reduction of viability (≤ of 12%) in the HepG2 cell line at all the tested concentrations (FIG. 5).

The S enantiomer of the B4a molecule has a slight concentration-independent cytotoxic effect in HepG2 cells (evident only at 25 micrograms/mL), while the R-enantiomer does not determine an apparent reduction in cell viability. HepG2 cells, as expected, is subject to a mortality of 20% after treatment with 100 micrograms/mL of linezolid.

Oxidative Phosphorylation (OXPHOS) Assay

This assay (Nadaciva S. et al., 2010) is used to monitor the level of mitochondrial protein synthesis of some key proteins in the process of oxidative phosphorylation of eukaryotic cells, comparing it with the level of synthesis of mitochondrial proteins encoded by nuclear DNA. This study allows us to analyze the effects of A4bS on the proteins encoded by mitochondrial DNA (mtDNA).

Figure 6:
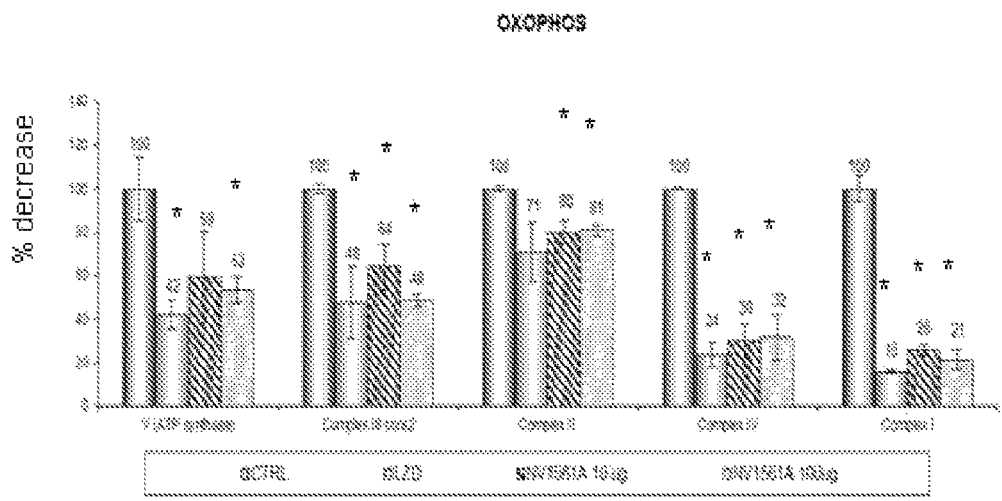
FIG. 6: Results of OXPHOS assay on HepG2 cells treated with A4aS and A4bS compounds (compounds 22 and 23 of Table 1) in the form of their respective S enantiomers.
Figure 7:
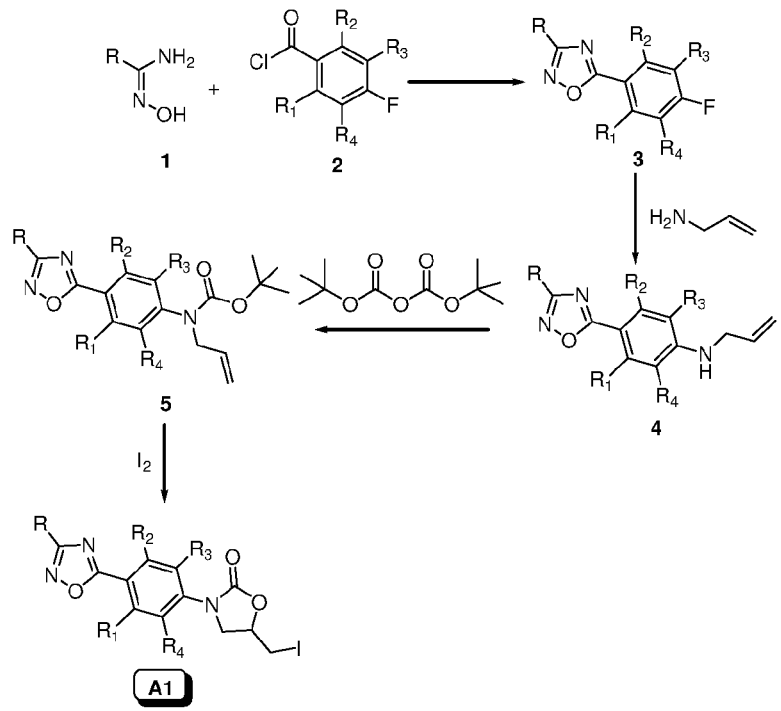
FIG. 7: Scheme 1 of chemical synthesis of compounds 1-5 and A1.
Figure 8:
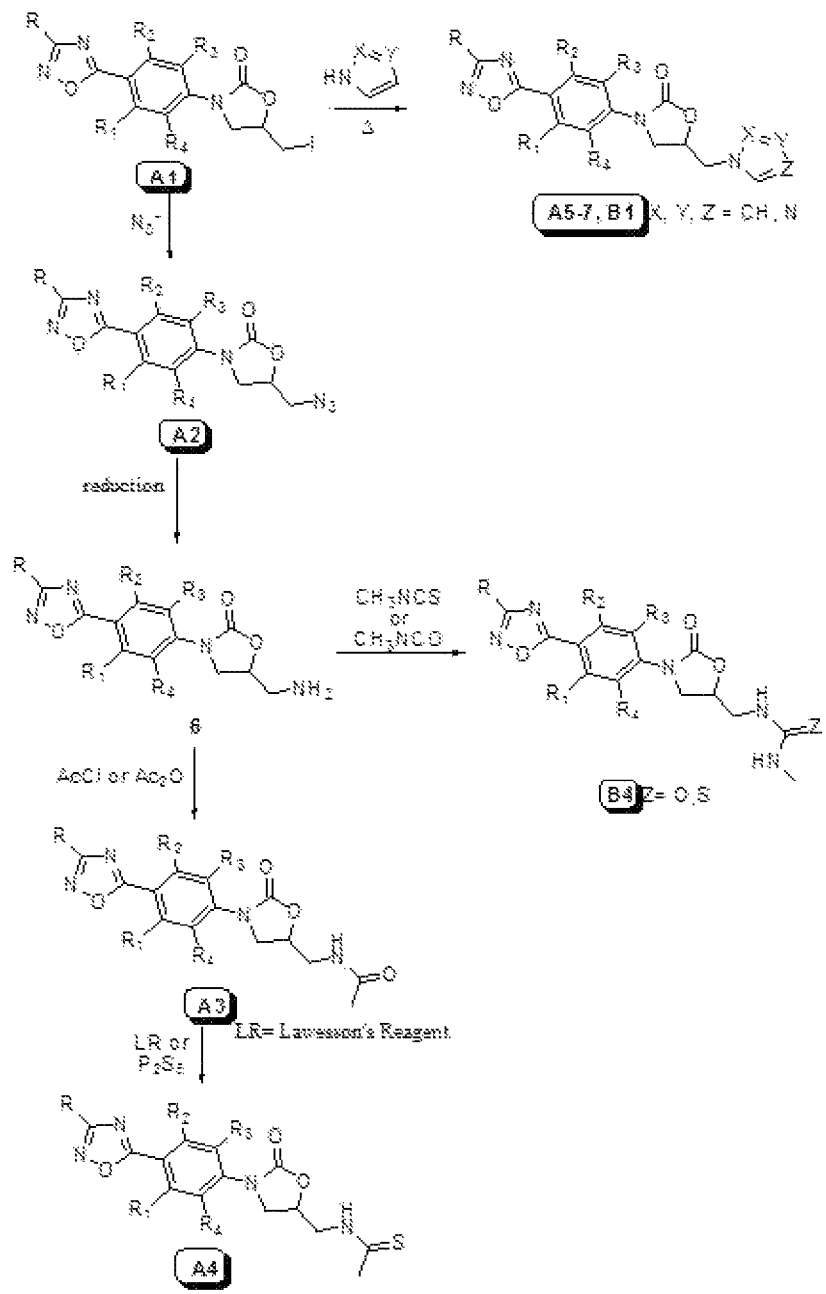
FIG. 8: Scheme 2 of chemical synthesis of A and B compounds.
Figure 9:
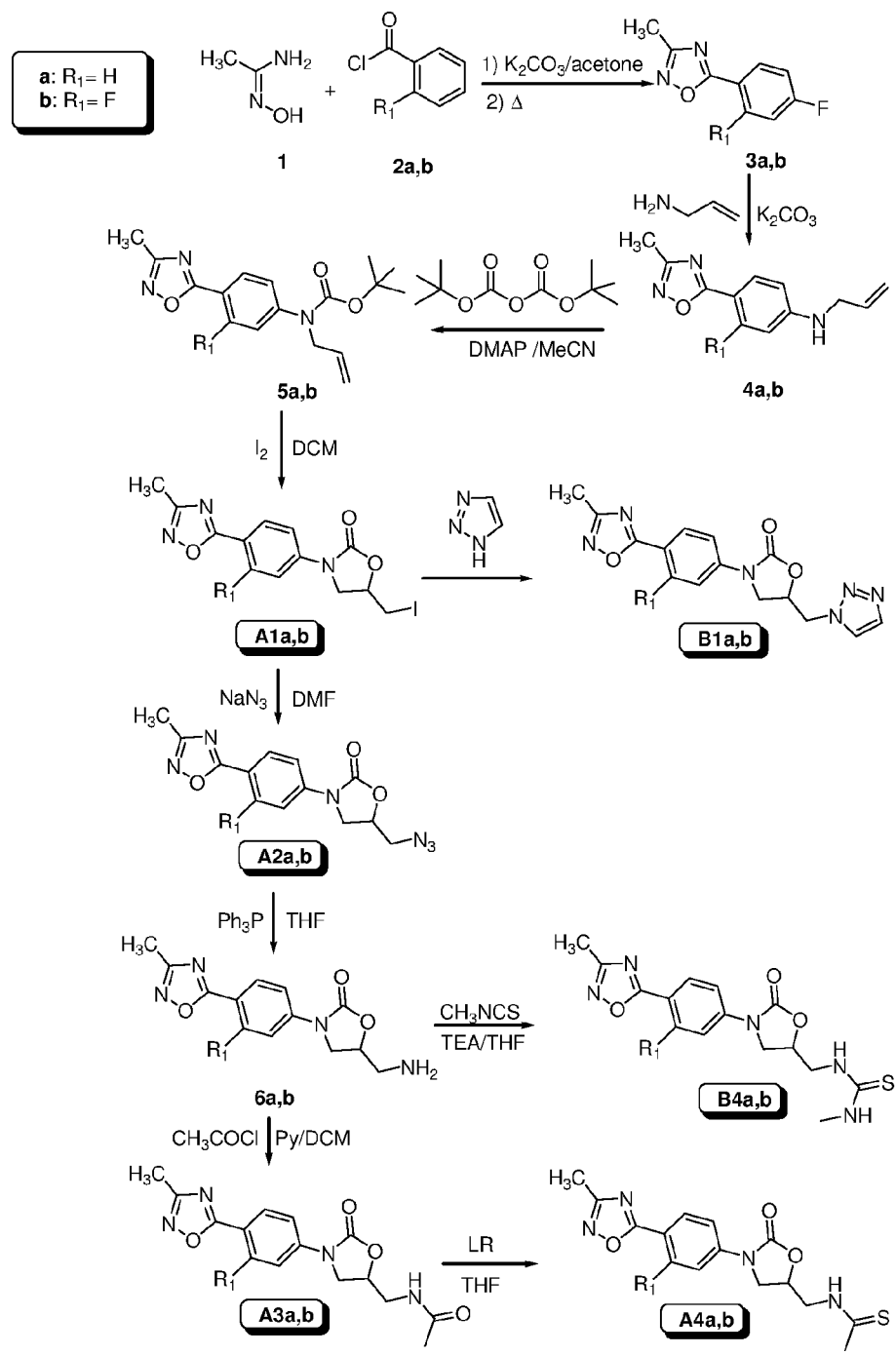
FIG. 9: Scheme 3 of chemical synthesis of the compounds of interest A and B.

The results, shown in FIG. 6, confirm that linezolid (100 □g/mL) acts negatively on mitochondrial protein synthesis. In fact, the proteins of complex I, III (core 2) and IV (synthesized by mtDNA) undergo a significant decrease after the treatment of linezolid. In parallel, one can compare the A4bS molecule (10-100 µg/mL), which as linezolid, causing a reduction of the synthesis of proteins of complex I and IV with respect to the control (non-treated cells). However, it is to be noted that the decrease in the protein synthesis induced by the compound A4bS is of a lower entity than that induced by linezolid, such an effect highlights a decrease of the side effect linked to the reversible myelosuppression. The results reported in FIG. 6 were obtained as followed: the levels of the proteins encoded by the mitochondrial DNA (mtDNA) synthesized on mitochondrial ribosome (Complex IV, Complex I) and of the proteins encoded by the nuclear DNA synthesized on the ribosome in the cytosol (Complex II subunit V complex), and imported in mitochondria, were analyzed by MitoProfile 6 Total OXPHOS human WB antibody after treatment of HepG2 cells (human hepatocellular carcinoma cells) with the compound A4bS. The data represent the mean±SEM of three separate experiments performed in triplicate. Statistical significance is obtained by the Student's test compared to the compounds.

*=p<0.05; **=p<0.01.

Chemical Synthesis

Melting points were determined on a Reichart-Thermovar hotstage apparatus and are uncorrected. IR spectra (Nujol) were determined with a Shimadzu FTIR-8300 instrument; H NMR spectra were recorded on a Bruker 300 Avance spectrometer using TMS as an internal standard. Flash chromatography was performed by using silica gel (0.040-0.063 mm) and mixtures of ethyl acetate and petroleum ether (fraction boiling in the range of 40-60° C.) in various ratios. The purity of compounds, in all cases higher than 95%, has been checked by both NMR and HPLC analyses. Separation of racemates was performed by means of HPLC with chiral stationary phase (Daicel, Chiralpak-IA), by using hexane-iPrOH (70:30) as mobile phase, and 1 mL/min flux. In every case an ee>99% was obtained.

The Most Interesting Compounds:

A1a (compound 148 table 1), A1b (compound 149 table 1), A3a (compound 15 table 1), A3b (compound 16 table 1), A4a (compound 22 table 1), A4b (compound 23 table 1), B1a (compound 155 table 1), B1b (compound 156 table 1), B4a (compound 106 table 1), B4b (compound 107 table 1); reported in table 2 (group A) and 3 (group B) and corresponding intermediates 1-6, were obtained accordingly to general methodologies reported on schemes 1 and 2, following specifications indicated below and on scheme 3.

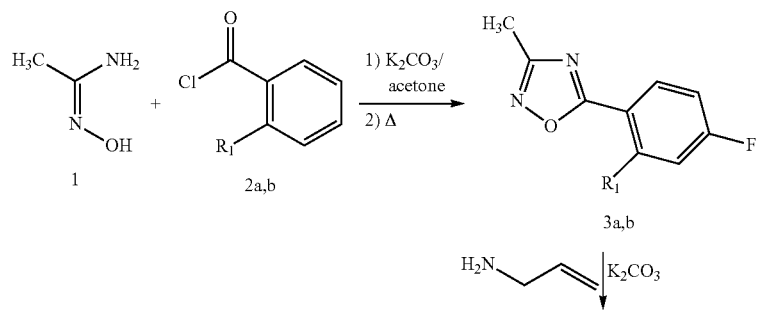

Scheme 3

-continued
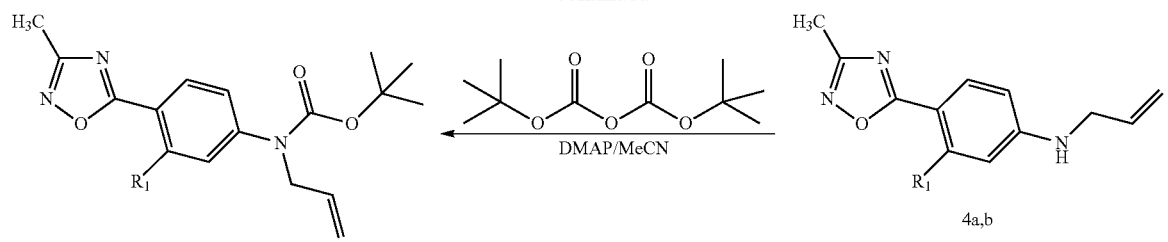
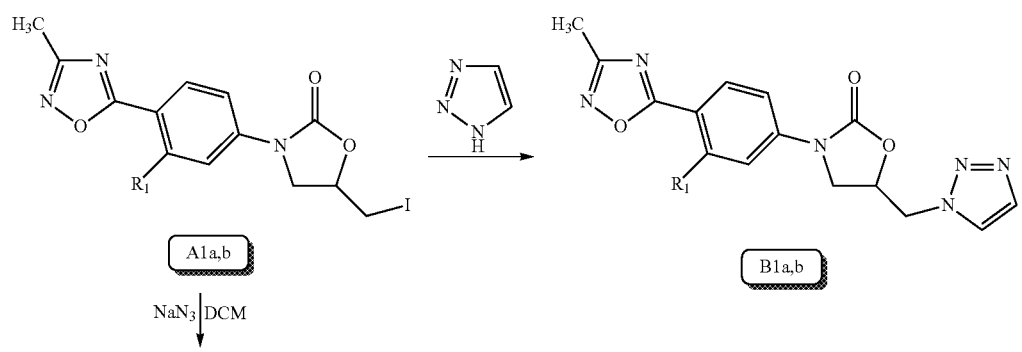
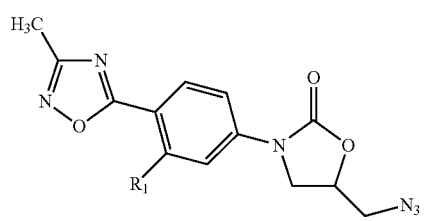
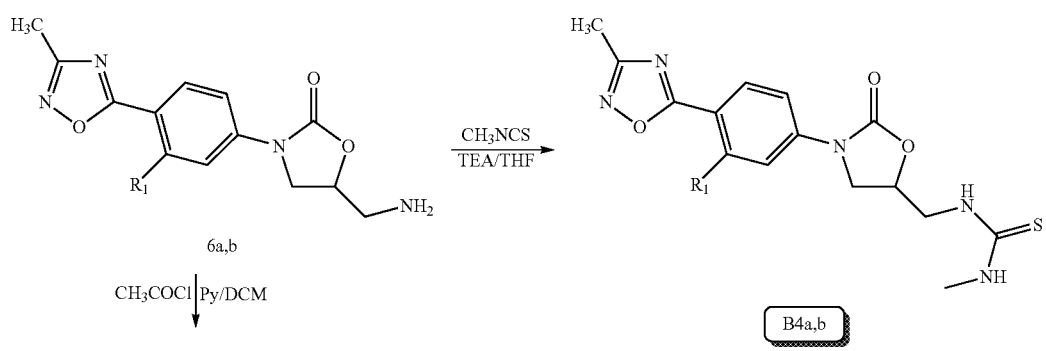

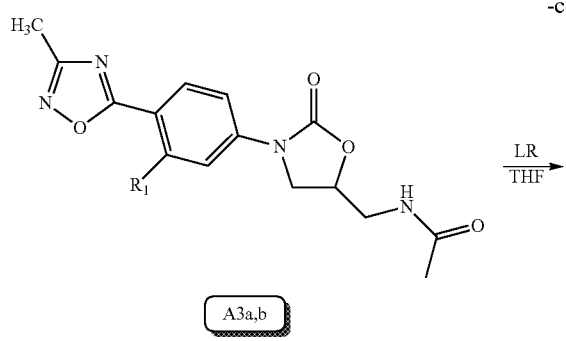

A3a,b

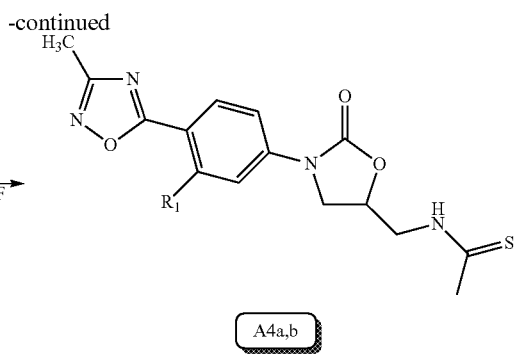

A4a,b a: R₁ = H
b: R₁ = F

General Procedure for the Preparation of Compounds 3a,b

A solution of hydroxylamine hydrochloride (1.00 g, 14.4 mmol) and NaOH (0.57 g, 14.4 mmol) in water (5 mL) was added (in about 15 minutes) to 15 mL of CH₃CN. The reaction mixture was stirred at room temperature for 24 hours. The solvent was removed under reduced pressure and the residue treated with ethanol; the resulting suspension was filtered and the solvent was removed under reduced pressure producing 1.659 g of acetamidoxime 1 (77%). Then, either 4-fluorobenzoyl (2a) chloride or 2,4-difluorobenzoyl chloride (2b) (14.8 mmol) were added to a solution of 1 (1.00 g; 13.5 mmol) in Acetone (35 mL) containing also K₂CO₃ (2.05 g, 14.8 mmol). The mixture was stirred at room temperature for about 90 minutes after which the solvent was removed under reduced pressure. The residue was treated with water and the solid precipitate was collected by filtration. The obtained O-acylamidoxime was heated, without any further purification, at about 130° C. for 90 minutes in a sealed tube. The obtained residue was chromatographed yielding the corresponding 1,2,4-oxadiazoles 3a and 3b.

3-methyl-5-(4'-fluorophenyl)-1,2,4-oxadiazole (3a): Yield (72%); mp 80.0-81.0° C.; ¹H NMR (300 MHz; CDCl₃) 2.45 (s, 3H, Me); 7.16-7.23 (m, 2H, Ar); 8.08-8.14 (m, 2H, Ar). Anal. Found (calc) for C₉H₇FN₂O (%): C, 60.65 (60.67); H, 3.90 (3.96); N, 15.70 (15.72).

3-methyl-5-(2',4'-difluorophenyl)-1,2,4-oxadiazole (3b): Yield (72%); mp 57.0-60.0° C.; ¹H-NMR (300 MHz; CDCl₃) 2.46 (s, 3H, Me); 6.95-7.07 (m, 2H, Ar); 8.04-8.14 (m, 1H, Ar). Anal. Found (calc) for C₉H₆F₂N₂O (%): C, 55.15 (55.11); H, 3.10 (3.08); N, 14.25 (14.28).

Preparation of N-allyl-4-(3'-methyl-1,2,4-oxadiazol-5'-yl)-aniline (4a)

Compound 3a (0.61 g; 3.43 mmol) was heated, with allylamine (3.0 mL; 2.28 g; 40.0 mmol) and K₂CO₃ (2.00 g; 14.5 mmol), at about 60° C. for 8 days. The reaction mixture was treated with water and extracted with EtOAc. The organic layers were collected, dried over anhydrous Na₂SO₄, filtered and the solvent removed. The residue was chromatographed yielding compound 3a: Yield (54%); mp 63.9-65.5° C.; IR (Nujol) 3335 (NH), 1607 (C=N) cm⁻¹; ¹H-NMR (300 MHz; DMSO-d₆) 2.31 (s, 3H, Me); 3.76-3.79 (m, 2H, CH₂); 5.12 (dd, 1H, J₁=10.5 Hz, J₂=1.8 Hz, —CH=CH₂); 5.22 (dd, 1H, J₁=17.1 Hz, J₂=1.8 Hz, —CH=CH₂); 5.82-5.93 (m, 1H, —CH=CH₂); 6.68 (d, 2H, J=9.0 Hz, Ar); 6.87 (t, 1H, J=5.7 Hz, NH, exch. with D₂O); 7.76 (d, 2H, J=9.0 Hz, Ar). Anal. Found (calc) for C₁₂H₁₃N₃O (%): C, 66.95 (66.96); H, 6.10 (6.09); N, 19.45 (19.52).

Preparation of N-allyl-3-fluoro-4-(3'-methyl-1,2,4-oxadiazol-5'-yl)-aniline (4b)

To a solution of 3b (0.86 g; 4.38 mmol) in DMF (2.0 mL) was added allylamine (1.64 mL; 1.25 g; 22.0 mmol). The reaction mixture was stirred for 2 days, after which the solution was treated with water and extracted with EtOAc. The organic layers were collected, dried over anhydrous Na₂SO₄, filtered and the solvent removed. The residue was chromatographed yielding compound 4b: Yield (49%); mp 57.9-59.9° C.; IR (Nujol) 3335 (NH), 1626 (C=N) cm⁻¹; ¹H-NMR (300 MHz; DMSO-d₆) 2.34 (s, 3H, Me); 3.77-3.81 (m, 2H, CH₂); 5.13 (dd, 1H, J₁=13.2 Hz, J₂=1.2 Hz, —CH=CH₂); 5.23 (dd, 1H, J₁=17.4 Hz, J₂=1.2 Hz, —CH=CH₂); 5.81-5.93 (m, 1H, —CH=CH₂); 6.46 (dd, 1H, J₁=14.4 Hz, J₂=1.8 Hz, Ar); 6.56 (dd, 1H, J₁=8.7 Hz, J₂=1.8 Hz, Ar); 7.17-7.21 (bs, 1H, NH, exch. with D₂O); 7.72-7.77 (m, 1H, Ar). Anal. Found (calc) for C₁₂H₁₂FN₃O (%): C, 61.80 (61.79); H, 5.10 (5.19); N, 18.15 (18.02).

General Procedure for the Preparation of Compounds 5a,b

Either compound 4a or 4b (2.15 mmol) were dissolved in CH₃CN (25 mL); di-(t-butyl)-dicarbonate (0.51 g; 2.36 mmol) and 4-dimethylaminopyridine (0.29 g; 2.36 mmol) were added and the mixture was stirred for 2 days or 2.5 hours, respectively. The solvent was removed under reduced pressure and the obtained residue was chromatographed yielding the corresponding compounds 5a and 5b.

tert-butyl N-allyl-(4-(3'-methyl-1,2,4-oxadiazol-5'-yl)-phenyl)-carbamate (5a): oil; Yield (73%); IR (Nujol) 1711 (NCO₂), 1614 (C=N) cm⁻¹; ¹H-NMR (300 MHz; CDCl₃) 1.27 (s, 9H, t-Bu); 2.25 (s, 3H, Me); 4.10 (d, 2H, J=5.1 Hz, CH₂); 4.95-4.97 (m, 1H, —CH=CH₂); 4.99-5.01 (m, 1H, —CH=CH₂); 5.67-5.78 (m, 1H, —CH=CH₂); 7.23 (d, 2H, J=9.0 Hz, Ar); 7.84 (d, 2H, J=9.0 Hz, Ar). Anal. Found (calc) for C₁₇H₂₁N₃O₃ (%): C, 64.70 (64.74); H, 6.80 (6.71); N, 13.35 (13.32).

tert-butyl N-allyl-(3-fluoro-4-(3'-methyl-1,2,4-oxadiazol-5'-yl)-phenyl)-carbamate (5b): oil; Yield (72%); IR (Nujol) 1713 (NCO₃), 1615 (C=N) cm⁻¹; ¹H-NMR (300 MHz; CDCl₃) 1.53 (s, 9H, t-Bu); 2.53 (s, 3H, Me); 4.36 (d, 2H, J=5.1 Hz, CH₂); 5.21-5.28 (m, 2H, —CH=CH₂); 5.91-6.02 (m, 1H, —CH=CH₂); 7.28-7.36 (m, 2H, Ar); 8.02-8.08 (m, 1H, Ar). Anal. Found (calc) for C₁₇H₂₀FN₃O₃ (%): C, 61.25 (61.25); H, 6.10 (6.05); N, 12.65 (12.61).

General Procedure for the Preparation of Compounds A1a,b

To a solution of 1.70 mmol of either compound 5a or 5b in CH₂Cl₂ (10 mL) was added I₂ sublimate (1.29 g; 5.10 mmol). The solution was stirred for 24 hours, after which the reaction was treated with a solution of Na₂SO₃; the organic layer was dried over anhydrous Na₂SO₄, filtered and the solvent removed. The residue was chromatographed yielding the corresponding compounds A1a and A1b.

3-(4'-(3"-methyl-1,2,4-oxadiazol-5"-yl)-phenyl)-5-(iodomethyl)-oxazolidin-2-one (A1a): Yield (89%); mp 145.0-147.0° C.; IR (Nujol) 1763 ($NCO_2$), 1618 (C=N) $cm^{-1}$; $^1$H-NMR (300 MHz; DMSO-$d_6$) 2.47 (s, 3H, Me); 3.62-3.73 (m, 2H, $CH_2$—I); 3.80 (dd, 1H, $J_1$=9.3 Hz, $J_2$=6.0 Hz, $C_4$—H); 4.34 (dd, 1H, $J_1$=9.3 Hz, $J_2$=9.0 Hz, $C_4$—H); 4.81-4.90 (m, 1H, $C_5$—H); 7.88 (d, 2H, J=9.0 Hz, Ar); 8.17 (d, 2H, J=9.0 Hz, Ar). Anal. Found (calc) for $C_{13}H_{12}IN_3O_3$ (%): C, 40.55 (40.54); H, 3.15 (3.14); N, 10.85 (10.91).

3-(3'-fluoro-4'-(3"-methyl-1,2,4-oxadiazol-5"-yl)-phenyl)-5-(iodomethyl)-oxazolidin-2-one (A1b): Yield (76%); mp 148.0-149.0° C.; IR (Nujol) 1743 ($NCO_2$), 1637 (C=N) $cm^{-1}$; $^1$H-NMR (300 MHz; DMSO-$d_6$) 2.48 (s, 3H, Me); 3.61-3.72 (m, 2H, $CH_2$—I); 3.81 (dd, 1H, $J_1$=9.6 Hz, $J_2$=6.0 Hz, $C_4$—H); 4.33 (dd, 1H, $J_1$=9.6 Hz, $J_2$=9.0 Hz, $C_4$—H); 4.83-4.93 (m, 1H, $C_5$—H); 7.68 (dd, 1H, $J_1$=8.7 Hz, $J_2$=2.1 Hz, Ar); 7.80 (dd, 1H, $J_1$=13.8 Hz, $J_2$=2.1 Hz, Ar); 8.16 (dd, 1H, $J_1$=8.7 Hz, $J_2$=8.5 Hz, Ar). Anal. Found (calc) for $C_{13}H_{11}FIN_3O_3$ (%): C, 38.75 (38.73); H, 2.55 (2.75); N, 10.35 (10.42).

General Procedure for the Preparation of Compounds A2a,b

To a solution of 0.75 mmol of compound A1a or A1b in DMF (6 mL) was added $NaN_3$ (0.39 g; 6.00 mmol). The solution was stirred for 24 hours, after which the reaction was treated with water and extracted with EtOAc; the organic layers were dried over anhydrous $Na_2SO_4$, filtered and the solvent removed. The residue was chromatographed yielding the corresponding compounds A2a and A2b.

3-(4'-(3"-methyl-1,2,4-oxadiazol-5-yl)-phenyl)-5-(azidometil)-oxazolidin-2-one (A2a): Yield (94%); mp 133.9-135.0° C.; IR (Nujol) 2095 ($N_3$), 1765 ($NCO_2$), 1727 ($NCO_2$), 1618 (C=N) $cm^{-1}$; $^1$H-NMR (300 MHz; DMSO-$d_6$) 2.46 (s, 3H, Me); 3.75-3.88 (m, 2H, $CH_2$—$N_3$); 3.92 (dd, 1H, $J_1$=9.3 Hz, $J_2$=6.0 Hz, $C_4$—H); 4.28 (t, 1H, J=9.3 Hz, $C_4$—H); 4.96-5.03 (m, 1H, $C_5$—H); 7.86 (d, 2H, J=9.0 Hz, Ar); 8.16 (d, 2H, J=9.0 Hz, Ar). Anal. Found (calc) for $C_{13}H_{12}N_6O_3$ (%): C, 52.05 (52.00); H, 4.10 (4.03); N, 27.85 (27.99).

3-(3'-fluoro-4'-(3"-methyl-1,2,4-oxadiazol-5-yl)-phenyl)-5-(azidometil)-oxazolidin-2-one (A2b): Yield (99%); mp 126.2-127.7° C.; IR (Nujol) 2107 ($N_3$), 1758 ($NCO_2$), 1743 ($NCO_2$), 1630 (C=N) $cm^{-1}$; $^1$H-NMR (300 MHz; DMSO-$d_6$) 2.41 (s, 3H, Me); 3.69-3.82 (m, 2H, $CH_2$—$N_3$); 3.86 (dd, 1H, $J_1$=9.3 Hz, $J_2$=6.0 Hz, $C_4$—H); 4.21 (t, 1H, J=9.3 Hz, $C_4$—H); 4.91-4.99 (m, 1H, $C_5$—H); 7.60 (dd, 1H, $J_1$=9.0 Hz, $J_2$=1.8 Hz, Ar); 7.72 (dd, 1H, $J_1$=13.5 Hz, $J_2$=1.8 Hz, Ar); 8.08-8.14 (m, 1H, Ar). Anal. Found (calc) for $C_{13}H_{11}FN_6O_3$ (%): C, 49.10 (49.06); H, 3.50 (3.48); N, 26.45 (26.41).

General Procedure for the Preparation of Compounds 6a,b

To a solution of 0.45 mmol of compound A2a or A2b in THF (15 mL) was added $PPh_3$ (0.16 g; 0.60 mmol). The solution was stirred for about 90 minutes, after which 100 l of distilled water was added and the resulting mixture was refluxed for 4 hours. The THF was removed under reduced pressure, the resulting residue was neutralized with hydrochloric acid and extracted with EtOAc. A solution of NaOH (pH~9) was added to the aqueous phase, which was extracted with EtOAc; the organic layers were dried over anhydrous $Na_2SO_4$, filtered and the solvent removed, yielding the corresponding compounds 6a and 6b.

3-(4'-(3"-methyl-1,2,4-oxadiazol-5-yl)-phenyl)-5-(aminomethyl)-oxazolidin-2-one (6a): Yield (66%); mp 139.3-141.3° C.; IR (Nujol) 3390 (NH), 3361 (NH), 1748 ($NCO_2$), 1616 (C=N) $cm^{-1}$; $^1$H-NMR (300 MHz; DMSO-$d_6$) 2.22 (bs, 2H, $NH_2$, exch. with $D_2O$); 2.39 (s, 3H, Me); 2.77-2.91 (m, 2H, $CH_2$—$NH_2$); 3.94 (dd, 1H, $J_1$=9.0 Hz, $J_2$=6.3 Hz, $C_4$—H); 4.13 (t, 1H, J=9.0 Hz, $C_4$—H); 4.61-4.70 (m, 1H, $C_5$—H); 7.80 (d, 2H, J=9.0 Hz, Ar); 8.09 (d, 2H, J=9.0 Hz, Ar). Anal. Found (calc) for $C_{13}H_{14}N_4O_3$ (%): C, 56.90 (56.93); H, 5.15 (5.14); N, 20.45 (20.43).

3-(3'-fluoro-4'-(3"-methyl-1,2,4-oxadiazol-5-yl)-phenyl)-5-(aminomethyl)-oxazolidin-2-one (6b): Yield (88%); mp 137.0-140.0° C.; IR (Nujol) 3372 (NH), 1743 ($NCO_2$), 1630 (C=N) $cm^{-1}$; $^1$H-NMR (300 MHz; DMSO-$d_6$) 2.21 (bs, 2H, $NH_2$, exch. with $D_2O$); 2.41 (s, 3H, Me); 2.77-2.91 (m, 2H, $CH_2$—$NH_2$); 3.93 (dd, 1H, $J_1$=9.3 Hz, $J_2$=6.3 Hz, $C_4$—H); 4.13 (t, 1H, J=9.0 Hz, $C_4$—H); 4.63-4.71 (m, 1H, $C_5$—H); 7.60 (dd, 1H, $J_1$=9.0 Hz, $J_2$=2.1 Hz, Ar); 7.73 (dd, 1H, $J_1$=10.8 Hz, $J_2$=2.1 Hz, Ar); 8.08-8.14 (m, 1H, Ar). Anal. Found (calc) for $C_{13}H_{13}FN_4O_3$ (%): C, 53.40 (53.42); H, 4.45 (4.48); N, 19.25 (19.17).

General Procedure for the Preparation of Compounds A3a,b.

Acetyl chloride (40 µl; 44 mg; 0.56 mmol) was added to a solution of either compound A3a or A3b (0.28 mmol) in $CH_2Cl_2$ (3 mL) containing also pyridine (1 mL; 0.97 g; 12.3 mmol). The solution was stirred for 30 minutes after which the solvent was removed and the residue treated with HCl 1M (20 mL) and extracted with EtOAc; the organic layers were dried over anhydrous $Na_2SO_4$, filtered and the solvent removed. The residue was chromatographed yielding the corresponding compounds A3a and A3b.

3-(4'-(3"-methyl-1,2,4-oxadiazol-5-yl)-phenyl)-5-(N-acetylaminomethyl)-oxazolidin-2-one (A3a): Yield (58%); mp 214.0-216.0° C.; IR (Nujol) 3257 (NH), 1751 ($NCO_2$), 1646 (amide), 1616 (C=N) $cm^{-1}$; $^1$H-NMR (300 MHz; DMSO-$d_6$) 1.89 (s, 3H, COMe); 2.46 (s, 3H, Me); 3.50 (t, 2H, J=5.7 Hz, $CH_2$—NHCOMe); 3.88 (dd, 1H, $J_1$=9.0 Hz, $J_2$=6.6 Hz, $C_4$—H); 4.25 (t, 1H, J=9.0 Hz, $C_4$—H); 4.79-4.87 (m, 1H, $C_5$—H); 7.84 (d, 2H, J=8.7 Hz, Ar); 8.16 (d, 2H, J=8.7 Hz, Ar); 8.32 (t, 1H, J=5.7 Hz, NH, exch. with $D_2O$); $^{13}$C-NMR (75 MHz; DMSO-$d_6$) 11.4, 22.6, 41.5, 47.2, 72.0, 118.1 (overlapped signals), 128.9, 142.6, 154.1, 167.7, 170.2, 174.5. Anal. Found (calc) for $C_{15}H_{16}N_4O_4$ (%): C, 56.95 (56.96); H, 5.05 (5.10); N, 17.85 (17.71).

3-(3'-fluoro-4'-(3"-methyl-1,2,4-oxadiazol-5-yl)-phenyl)-5-(N-acetylaminomethyl)-oxazolidin-2-one (A3b): Yield (62%); mp 184.0-186.0° C.; IR (Nujol) 3343 (NH), 1751 ($NCO_2$), 1666 (amide), 1628 (C=N) $cm^{-1}$; $^1$H-NMR (300 MHz; DMSO-$d_6$) 1.89 (s, 3H, COMe); 2.48 (s, 3H, Me); 3.50 (t, 2H, J=5.4 Hz, $CH_2$—NHCOMe); 3.88 (dd, 1H, $J_1$=9.3 Hz, $J_2$=6.3 Hz, $C_4$—H); 4.25 (t, 1H, J=9.0 Hz, $C_4$—H); 4.81-4.88 (m, 1H, $C_5$—H); 7.64 (dd, 1H, $J_1$=9.0 Hz, $J_2$=1.8 Hz, Ar); 7.77 (dd, 1H, $J_1$=13.8 Hz, $J_2$=1.8 Hz, Ar); 8.15-8.21 (m, 1H, Ar), 8.31 (m, 1H, NH, exch. with $D_2O$); $^{13}$C-NMR (75 MHz; DMSO-$d_6$) 11.32, 22.6, 41.5, 47.3, 72.2, 105.7 (d, $J_{C-F}$=32 Hz), 106.2 (d, $J_{C-F}$=14 Hz), 114.1, 131.4, 144.3 (d, $J_{C-F}$=14 Hz), 153.9, 160.4 (d, $J_{C-F}$=305 Hz), 167.5, 170.2, 171.6. Anal. Found (calc) for $C_{15}H_{15}FN_4O_4$ (%): C, 53.90 (53.89); H, 4.65 (4.52); N, 16.65 (16.76).

General Procedure for the Preparation of Compounds A4a,b

The Lawesson's reagent (0.2 g; 0.49 mmol) was added to a solution of either A3a or A3b (0.49 mmol) in THF (14 mL). The reaction mixture was refluxed for 2 hours, after which the solvent was removed under reduced pressure. The residue was chromatographed yielding the corresponding compounds A4a and A4b.

3-(4'-(3"-methyl-1,2,4-oxadiazol-5-yl)-phenyl)-5-(N-thioacetylaminomethyl)-oxazolidin-2-one (A4a): Yield (77%); mp 199.4-201.0° C.; IR (Nujol) 3217 (NH), 1721 ($NCO_2$), 1618 (thioamide) $cm^{-1}$; $^1$H-NMR (300 MHz; DMSO-$d_6$) 2.47 (s, 3H, Me); 2.51 (s, 3H, CSMe); 3.95-4.03 (m, 3H, overlapped signals); 4.28-4.34 (m, 1H, $C_4$—H); 5.01-5.11 (m, 1H, $C_5$—H); 7.85 (d, 2H, J=9.0 Hz, Ar); 8.18 (d, 2H, J=9.0 Hz, Ar); 10.45 (bs, 1H, NH, exch. with $D_2O$). Anal. Found (calc) for $C_{15}H_{16}N_4O_3S$ (%): C, 54.15 (54.20); H, 4.85 (4.85); N, 16.90 (16.86).

3-(3'-fluoro-4'-(3''-methyl-1,2,4-oxadiazol-5-yl)-phenyl)-5-(N-thioacetylaminomethyl)-oxazolidin-2-one (A4b): Yield (93%); mp 166.5-167.7° C.; IR (Nujol) 3262 (NH), 1746 (NCO$_2$), 1633 (thioamide) cm$^{-1}$; $^1$H-NMR (300 MHz; DMSO-d$_6$) 2.48 (s, 3H, Me); 2.51 (s, 3H, CSMe); 3.94-4.00 (m, 3H, overlapped signals); 4.28-4.34 (m, 1H, C$_4$—H); 5.04-5.12 (m, 1H, C$_5$—H); 7.65 (dd, 1H, J$_1$=9 Hz, J$_2$=1.8 Hz, Ar); 7.78 (dd, 1H, J$_1$=13.5 Hz, J$_2$=1.8 Hz, Ar); 8.16-8.22 (m, 1H, Ar); 10.45 (bs, 1H, NH exch. with D$_2$O). Anal. Found (calc) for C$_{15}$H$_{14}$FN$_4$O$_3$S (%): C, 51.35 (51.42); H, 4.30 (4.32); N, 16.05 (15.99).

General Procedure for the Preparation of Compounds B1a,b

In a glass tube, to 0.45 mmol of compound A1a or A1b was added 1,2,3-triazole (0.124 g; 1.8 mmol). The mixture was heated until complete consumption of the starting material monitored by TLC. The residue was chromatographed yielding the corresponding compounds B1a and B1b.

((3-(4-(3-methyl-1,2,4-oxadiazol-5-yl)phenyl)-oxazolidin-2-on-5-yl)methyl)-4,5-dihydro-1H-1,2,3-triazole (B1a): Yield (73%); mp 208-210° C.; IR (Nujol) 1751 cm$^{-1}$; $^1$H-NMR (300 MHz; CDCl$_3$) 2.46 (s, 3H), 4.03 (dd, J$_1$=6.3 Hz, J$_2$=9.3 Hz, 1H), 4.25 (dd, J$_1$=9.3 Hz, J$_2$=9.0 Hz, 1H), 4.82-4.83 (m, 2H), 5.08-5.14 (m, 1H), 7.59 (d, J=9.0 Hz, 1H), 7.75 (s, 1H), 7.80 (s, 1H), 8.08 (d, J=9.0 Hz, 1H); Anal. Found (calc) for C$_{15}$H$_{14}$N$_6$O$_3$ (%): C, 55.30 (55.21); H, 4.39 (4.32); N, 25.69 (25.75).

((3-(3-fluoro-4-(3-methyl-1,2,4-oxadiazol-5-yl)phenyl)-oxazolidin-2-on-5-yl)methyl)-4,5-dihydro-1H-1,2,3-triazole (B1b): Yield (64%); mp 176.2-177.8° C.; IR (Nujol) 1751 cm$^{-1}$; $^1$H-NMR (300 MHz; CDCl$_3$) 2.48 (s, 3H), 4.03 (dd, J$_1$=9.3 Hz, J$_2$=6.0 Hz, 1H), 4.25 (dd, J$_1$=9.6 Hz, J$_2$=9.0 Hz, 1H), 4.82-4.83 (m, 2H), 5.15-5.30 (m, 1H), 7.27 (dd, J$_1$=8.3 Hz, J$_2$=1.8 Hz, 1H), 7.56 (dd, J$_1$=12.6 Hz, J$_2$=1.8 Hz, 1H), 7.75 (s, 1H), 7.79 (s, 1H), 8.02 (t, J=8.3 Hz, 1H); Anal. Found (calc) for C$_{15}$H$_{13}$FN$_6$O$_3$ (%): C, 52.37 (52.33); H, 3.85 (3.81); N, 24.47 (24.41).

General Procedure for the Preparation of Compounds B4a,b

To a solution of 0.55 mmol of compound 6a or 6b in THF (5 mL) was added CH$_3$NCS (0.041 mL; 0.60 mmol) and trietylamine (0.084 mL; 0.60 mmol). The solution was stirred for 3 hours at room temperature. The solvent was then removed under vacuum. The residue was chromatographed yielding the corresponding compounds B4a and B4b.

1-((3-(4-(3-methyl-1,2,4-oxadiazol-5-yl)phenyl)-oxazolidin-2-one-5-yl)methyl)-3-methylthiourea (B4a): Yield (80%); mp 189.4-191.8° C.; IR (Nujol) 3364, 1732 cm$^{-1}$; $^1$H-NMR (300 MHz; CDCl$_3$) 2.39 (s, 3H), 2.82 (bs, 3H), 3.82-4.00 (m, 3H), 4.20 (dd, J$_1$=8.7 Hz, J$_2$=6.0 Hz, 1H), 4.91 (bs, 1H), 7.77-7.80 (m, 3H), 8.09 (d, J=6.9 Hz, 2H); Anal. Found (calc) for C$_{15}$H$_{17}$N$_5$O$_3$S (%): C, 51.91 (51.86); H, 5.00 (4.93); N, 20.20 (20.16).

1-((3-(3-fluoro-4-(3-methyl-1,2,4-oxadiazol-5-yl)phenyl)-oxazolidin-2-one-5-yl)methyl)-3-methylthiourea (B4b): Yield (88%); mp 170.7-172.4° C.; IR (Nujol) 3370, 1739 cm$^{-1}$; $^1$H-NMR (300 MHz, DMSO) 2.48 (s, 3H), 2.89 (bs, 3H), 3.89-4.07 (m, 3H), 4.24-4.30 (m, 1H), 4.89 (bs, 1H), 7.74 (s, 1H), 7.79 (dd, J$_1$=13.5 Hz, J$_2$=2.1 Hz, 2H), 8.20 (t, J=9.0 Hz, 2H); Anal. Found (calc) for C$_{15}$H$_{16}$FN$_5$O$_3$S (%): C, 49.21 (49.31); H, 4.35 (4.41); N, 19.10 (19.17).

REFERENCES

[1] S. Tsiodras, H. S. Gold, G. Sakoulas, G. M. Eliopoulos, C. Wennersten, L. Venkataraman, R. C. Moellering, M. J. Ferraro, *Lancet* 2001, 358, 207-208.

[2] C. Auckland, L. Teare, F. Cooke, M. E. Kaufmann, M. Warner, G. Jones, K. Bamford, H. Ayles, A. P. Johnson, *J. Antimicrob. Chemother.* 2002, 50, 743-746.

[3] J. Seedat, G. Zick, I. Klare, C. Konstabel, N. Weiler, H. Sahly, *Antimicrob. Ag. Chemother.* 2006, 50, 4217-4219.

[4] S. Kelly, J. Collins, M. Maguire, C. Gowing, M. Flanagan, M. Donnelly, P. G. Murphy, *J. Antimicrob. Chemother.* 2008, 61, 901-907.

[5] J. V. N. Vara Prasad, *Curr. Op. Microbiol.* 2007, 10, 454-460.

[6] C. Farrerons Gallemi, 2005, US Patent 2005/0014806.

[7] L. B. Snyder, Z. Meng, R. Mate, S. V. D'Andrea, A. Marinier, et al.; *Bioorg. Med. Chem. Lett.,* 2004, 14, 4735-4739.

[8] A. Palumbo Piccionello, R. Musumeci, C. Cocuzza, C. G. Fortuna, A. Guarcello, P. Pierro, A. Pace, *Eur. J. Med. Chem.* 2012, 50, 441-448.

[9] A. Pace, P. Pierro, *Org. Biomol. Chem.* 2009, 7, 4337-4348.

[10] S. Buscemi, A. Pace, R. Calabrese, N. Vivona, P. Metrangolo, *Tetrahedron* 2001, 57, 5865-5871.

[11] S. Buscemi, A. Pace, A. Palumbo Piccionello, I. Pibiri, N. Vivona, *Heterocycles* 2004, 63, 1619-1628.

[12] A. Palumbo Piccionello, A. Pace, I. Pibiri, S. Buscemi, N. Vivona, *Tetrahedron* 2006, 62, 8792-8797.

[13] A. Palumbo Piccionello, A. Pace, P. Pierro, I. Pibiri, S. Buscemi, N. Vivona, *Tetrahedron* 2009, 65, 119-127.

[14] K. C. Grega, M. R. Barbachyn, S. J. Brickner, S. A. Mizsak, *J. Org. Chem.* 1995, 60, 5255-5261.

[15] H. Biswajit Das, H. Sonali Rudra, A. Songita Songita, P. Mohammad Salman, H. Ashok Rattan, 2008, US Patent 2008/0188470.

[16] Clinical and Laboratory Standards Institute. Methods for Dilution Antimicrobial Susceptibility Tests for Bacteria That Grow Aerobically; Approved Standard—Ninth Edition. 2011, M07-A9, 32, Wayne, Pa.

[17] E. C. Pirtle, *Am. J. Vet. Res.* 1966, 27, 747-749.

[18] D. P. Aden, A. Fogel, S. Plotkin, I. Damjanov, B. B. Knowles, *Nature* 1979, 282, 615-616.

[19] G. Pozzi, M. Guidi, F. Laudicina, M. Marazzi, L. Falcone, R. Betti, C. Crosti, E. Müller, G. E. Di Mattia, V. Locatelli, A. Torsello, *J. Endocrinol. Invest.* 2004, 27, 142-149.

[20] A. Bulbarelli, E. Lonati, E. Cazzaniga, M. Gregori, M. Masserini, *Mol. Cell. Neurosci.* 2009, 42, 75-80.

The invention claimed is:

1. A method of therapeutic treatment of infection by Gram-positive bacteria; wherein the Gram-positive bacteria are *Staphylococcus* spp, *Enterococcus* spp, or *Streptococcus* spp; comprising administering to a patient a pharmaceutically active amount of a pharmaceutical composition containing a compound having the general formula (I):

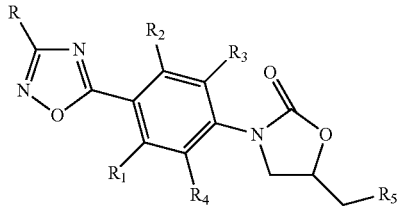

Formula (I)

as a racemic mixture or a pure enantiomer or a mixture enriched with either S or R enantiomer, wherein:
R=methyl, ethyl, or phenyl;
R$_{1-4}$=independently H, F, Cl, Br, CH$_3$, OH, or OCH$_3$;
R$_5$=I, —NCS, —NHC(X)CH$_3$ with X=O or S, —NHC(X)NHR$_7$ with X=O or S and R$_7$=H or C1-C3 alkyl, NHC(X)NHCOCH$_3$ with X=O or S, or heteroaryl.

2. The method of treatment according to claim 1, wherein the infection is caused by multi antibiotic-resistant bacteria.

3. The method of treatment according to claim 1, wherein at least one of substituents $R_1$, $R_2$, $R_3$ or $R_4$ is a fluorine atom, while the others are H.

4. The method of treatment according to claim 1, wherein $R_5$ is selected from the group consisting of: I, —NCS, NHC(=O)CH$_3$, NHC(=S)CH$_3$, —NHC(=O)CH$_2$F, —NHC(=S)CH$_2$F, —NHC(=O)CH$_2$Cl, —NHC(=S)CH$_2$Cl, —NHC(=S)NH$_2$, NHC(=O)NH$_2$, —NHC(=O)NHCH$_3$, —NHC(=S)NHCH$_3$, —NHC(=O)NHC$_2$H$_5$, —NHC(=S)NHC$_2$H$_5$, and 1,2,3 triazol-1-yl.

5. The method of treatment according to claim 1, wherein $R_5$ and R are selected from the group consisting of:
$R_5$ is NHC(=S)CH$_3$ and R is CH$_3$,
$R_5$ is NHC(=S)NHCH$_3$ and R is CH$_3$,
$R_5$ is NHC(=O)CH$_3$ and R is CH$_3$, and
$R_5$ is NHC(=S)NH$_2$ and R is CH$_3$.

6. The method of treatment according to claim 1, wherein the compound is in the form of pure S enantiomer or a mixture enriched with the S enantiomer.

7. The method of treatment according to claim 1, wherein the compound is selected from the group consisting of compounds of Table 1 below:

TABLE 1

|  | R | $R_1$ | $R_2$ | $R_3$ | $R_4$ | $R_5$ |
|---|---|---|---|---|---|---|
| 1 | Ph | H | H | H | H | NHC(=O)CH$_3$ |
| 2 | Ph | F | H | H | H | NHC(=O)CH$_3$ |
| 3 | Ph | F | F | H | H | NHC(=O)CH$_3$ |
| 4 | Ph | F | F | F | H | NHC(=O)CH$_3$ |
| 5 | Ph | F | F | F | F | NHC(=O)CH$_3$ |
| 6 | Ph | Cl | H | H | H | NHC(=O)CH$_3$ |
| 7 | Ph | Cl | Cl | H | H | NHC(=O)CH$_3$ |
| 8 | Ph | H | H | H | H | NHC(=S)CH$_3$ |
| 9 | Ph | F | H | H | H | NHC(=S)CH$_3$ |
| 10 | Ph | F | F | H | H | NHC(=S)CH$_3$ |
| 11 | Ph | Cl | H | H | H | NHC(=S)CH$_3$ |
| 12 | Ph | Cl | Cl | H | H | NHC(=S)CH$_3$ |
| 13 | Ph | F | F | F | H | NHC(=S)CH$_3$ |
| 14 | Ph | Br | H | H | H | NHC(=S)CH$_3$ |
| 15 (A3a) | CH$_3$ | H | H | H | H | NHC(=O)CH$_3$ |
| 16 (A3b) | CH$_3$ | F | H | H | H | NHC(=O)CH$_3$ |
| 17 | CH$_3$ | F | F | H | H | NHC(=O)CH$_3$ |
| 18 | CH$_3$ | F | F | F | H | NHC(=O)CH$_3$ |
| 19 | CH$_3$ | Cl | H | H | H | NHC(=O)CH$_3$ |
| 20 | CH$_3$ | Cl | Cl | H | H | NHC(=O)CH$_3$ |
| 21 | CH$_3$ | Br | H | H | H | NHC(=O)CH$_3$ |
| 22 (A4a) | CH$_3$ | H | H | H | H | NHC(=S)CH$_3$ |
| 23 (A4b) | CH$_3$ | F | H | H | H | NHC(=S)CH$_3$ |
| 24 | CH$_3$ | F | F | H | H | NHC(=S)CH$_3$ |
| 25 | CH$_3$ | Cl | H | H | H | NHC(=S)CH$_3$ |
| 26 | CH$_3$ | Cl | Cl | H | H | NHC(=S)CH$_3$ |
| 27 | CH$_3$ | F | F | F | H | NHC(=S)CH$_3$ |
| 28 | CH$_3$ | Br | H | H | H | NHC(=S)CH$_3$ |
| 29 | C$_2$H$_5$ | H | H | H | H | NHC(=O)CH$_3$ |
| 30 | C$_2$H$_5$ | F | H | H | H | NHC(=O)CH$_3$ |
| 31 | C$_2$H$_5$ | F | F | H | H | NHC(=O)CH$_3$ |
| 32 | C$_2$H$_5$ | F | F | F | H | NHC(=O)CH$_3$ |
| 33 | C$_2$H$_5$ | Cl | H | H | H | NHC(=O)CH$_3$ |
| 34 | C$_2$H$_5$ | Cl | Cl | H | H | NHC(=O)CH$_3$ |
| 35 | C$_2$H$_5$ | Br | H | H | H | NHC(=O)CH$_3$ |
| 36 | C$_2$H$_5$ | H | H | H | H | NHC(=S)CH$_3$ |
| 37 | C$_2$H$_5$ | F | H | H | H | NHC(=S)CH$_3$ |
| 38 | C$_2$H$_5$ | F | F | H | H | NHC(=S)CH$_3$ |
| 39 | C$_2$H$_5$ | Cl | H | H | H | NHC(=S)CH$_3$ |
| 40 | C$_2$H$_5$ | Cl | Cl | H | H | NHC(=S)CH$_3$ |
| 41 | C$_2$H$_5$ | F | F | F | H | NHC(=S)CH$_3$ |
| 42 | C$_2$H$_5$ | Br | H | H | H | NHC(=S)CH$_3$ |
| 43 | Ph | H | H | H | H | NHC(=O)NH$_2$ |
| 44 | Ph | F | H | H | H | NHC(=O)NH$_2$ |
| 45 | Ph | F | F | H | H | NHC(=O)NH$_2$ |
| 46 | Ph | F | F | F | H | NHC(=O)NH$_2$ |
| 47 | Ph | Br | H | H | H | NHC(=O)NH$_2$ |
| 48 | Ph | Cl | H | H | H | NHC(=O)NH$_2$ |
| 49 | Ph | Cl | Cl | H | H | NHC(=O)NH$_2$ |
| 50 | Ph | H | H | H | H | NHC(=S)NH$_2$ |
| 51 | Ph | F | H | H | H | NHC(=S)NH$_2$ |
| 52 | Ph | F | F | H | H | NHC(=S)NH$_2$ |
| 53 | Ph | Cl | H | H | H | NHC(=S)NH$_2$ |
| 54 | Ph | Cl | Cl | H | H | NHC(=S)NH$_2$ |
| 55 | Ph | F | F | F | H | NHC(=S)NH$_2$ |
| 56 | Ph | Br | H | H | H | NHC(=S)NH$_2$ |
| 57 | CH$_3$ | H | H | H | H | NHC(=O)NH$_2$ |
| 58 | CH$_3$ | F | H | H | H | NHC(=O)NH$_2$ |
| 59 | CH$_3$ | F | F | H | H | NHC(=O)NH$_2$ |
| 60 | CH$_3$ | F | F | F | H | NHC(=O)NH$_2$ |
| 61 | CH$_3$ | Cl | H | H | H | NHC(=O)NH$_2$ |
| 62 | CH$_3$ | Cl | Cl | H | H | NHC(=O)NH$_2$ |
| 63 | CH$_3$ | Br | H | H | H | NHC(=O)NH$_2$ |
| 64 (B3a) | CH$_3$ | H | H | H | H | NHC(=S)NH$_2$ |
| 65 (B3b) | CH$_3$ | F | H | H | H | NHC(=S)NH$_2$ |
| 66 | CH$_3$ | F | F | H | H | NHC(=S)NH$_2$ |
| 67 | CH$_3$ | Cl | H | H | H | NHC(=S)NH$_2$ |
| 68 | CH$_3$ | Cl | Cl | H | H | NHC(=S)NH$_2$ |
| 69 | CH$_3$ | F | F | F | H | NHC(=S)NH$_2$ |
| 70 | CH$_3$ | Br | H | H | H | NHC(=S)NH$_2$ |
| 71 | C$_2$H$_5$ | H | H | H | H | NHC(=O)NH$_2$ |
| 72 | C$_2$H$_5$ | F | H | H | H | NHC(=O)NH$_2$ |
| 73 | C$_2$H$_5$ | F | F | H | H | NHC(=O)NH$_2$ |
| 74 | C$_2$H$_5$ | F | F | F | H | NHC(=O)NH$_2$ |
| 75 | C$_2$H$_5$ | Cl | H | H | H | NHC(=O)NH$_2$ |
| 76 | C$_2$H$_5$ | Cl | Cl | H | H | NHC(=O)NH$_2$ |
| 77 | C$_2$H$_5$ | Br | H | H | H | NHC(=O)NH$_2$ |
| 78 | C$_2$H$_5$ | H | H | H | H | NHC(=S)NH$_2$ |
| 79 | C$_2$H$_5$ | F | H | H | H | NHC(=S)NH$_2$ |
| 80 | C$_2$H$_5$ | F | F | H | H | NHC(=S)NH$_2$ |
| 81 | C$_2$H$_5$ | Cl | H | H | H | NHC(=S)NH$_2$ |
| 82 | C$_2$H$_5$ | Cl | Cl | H | H | NHC(=S)NH$_2$ |
| 83 | C$_2$H$_5$ | F | F | F | H | NHC(=S)NH$_2$ |
| 84 | C$_2$H$_5$ | Br | H | H | H | NHC(=S)NH$_2$ |
| 85 | Ph | H | H | H | H | NHC(=O)NHCH$_3$ |
| 86 | Ph | F | H | H | H | NHC(=O)NHCH$_3$ |
| 87 | Ph | F | F | H | H | NHC(=O)NHCH$_3$ |
| 88 | Ph | F | F | F | H | NHC(=O)NHCH$_3$ |
| 89 | Ph | Br | H | H | H | NHC(=O)NHCH$_3$ |
| 90 | Ph | Cl | H | H | H | NHC(=O)NHCH$_3$ |
| 91 | Ph | Cl | Cl | H | H | NHC(=O)NHCH$_3$ |
| 92 | Ph | H | H | H | H | NHC(=S)NHCH$_3$ |
| 93 | Ph | F | H | H | H | NHC(=S)NHCH$_3$ |
| 94 | Ph | F | F | H | H | NHC(=S)NHCH$_3$ |
| 95 | Ph | Cl | H | H | H | NHC(=S)NHCH$_3$ |
| 96 | Ph | Cl | Cl | H | H | NHC(=S)NHCH$_3$ |
| 97 | Ph | F | F | F | H | NHC(=S)NHCH$_3$ |
| 98 | Ph | Br | H | H | H | NHC(=S)NHCH$_3$ |
| 99 | CH$_3$ | H | H | H | H | NHC(=O)NHCH$_3$ |
| 100 | CH$_3$ | F | H | H | H | NHC(=O)NHCH$_3$ |
| 101 | CH$_3$ | F | F | H | H | NHC(=O)NHCH$_3$ |
| 102 | CH$_3$ | F | F | F | H | NHC(=O)NHCH$_3$ |
| 103 | CH$_3$ | Cl | H | H | H | NHC(=O)NHCH$_3$ |
| 104 | CH$_3$ | Cl | Cl | H | H | NHC(=O)NHCH$_3$ |
| 105 | CH$_3$ | Br | H | H | H | NHC(=O)NHCH$_3$ |
| 106 (B4a) | CH$_3$ | H | H | H | H | NHC(=S)NHCH$_3$ |
| 107 (B4b) | CH$_3$ | F | H | H | H | NHC(=S)NHCH$_3$ |
| 108 | CH$_3$ | F | F | H | H | NHC(=S)NHCH$_3$ |
| 109 | CH$_3$ | Cl | H | H | H | NHC(=S)NHCH$_3$ |
| 110 | CH$_3$ | Cl | Cl | H | H | NHC(=S)NHCH$_3$ |
| 111 | CH$_3$ | F | F | F | H | NHC(=S)NHCH$_3$ |
| 112 | CH$_3$ | Br | H | H | H | NHC(=S)NHCH$_3$ |
| 113 | C$_2$H$_5$ | H | H | H | H | NHC(=O)NHCH$_3$ |
| 114 | C$_2$H$_5$ | F | H | H | H | NHC(=O)NHCH$_3$ |
| 115 | C$_2$H$_5$ | F | F | H | H | NHC(=O)NHCH$_3$ |
| 116 | C$_2$H$_5$ | F | F | F | H | NHC(=O)NHCH$_3$ |
| 117 | C$_2$H$_5$ | Cl | H | H | H | NHC(=O)NHCH$_3$ |
| 118 | C$_2$H$_5$ | Cl | Cl | H | H | NHC(=O)NHCH$_3$ |
| 119 | C$_2$H$_5$ | Br | H | H | H | NHC(=O)NHCH$_3$ |
| 120 | C$_2$H$_5$ | H | H | H | H | NHC(=S)NHCH$_3$ |
| 121 | C$_2$H$_5$ | F | H | H | H | NHC(=S)NHCH$_3$ |

TABLE 1-continued

|  | R | R$_1$ | R$_2$ | R$_3$ | R$_4$ | R$_5$ |
|---|---|---|---|---|---|---|
| 122 | C$_2$H$_5$ | F | F | H | H | NHC(=S)NHCH$_3$ |
| 123 | C$_2$H$_5$ | Cl | H | H | H | NHC(=S)NHCH$_3$ |
| 124 | C$_2$H$_5$ | Cl | Cl | H | H | NHC(=S)NHCH$_3$ |
| 125 | C$_2$H$_5$ | F | F | F | H | NHC(=S)NHCH$_3$ |
| 126 | C$_2$H$_5$ | Br | H | H | H | NHC(=S)NHCH$_3$ |
| 127 (B2a) | CH$_3$ | H | H | H | H | NCS |
| 128 (B2b) | CH$_3$ | F | H | H | H | NCS |
| 129 | CH$_3$ | F | F | H | H | NCS |
| 130 | CH$_3$ | Cl | H | H | H | NCS |
| 131 | CH$_3$ | Cl | Cl | H | H | NCS |
| 132 | CH$_3$ | F | F | F | H | NCS |
| 133 | CH$_3$ | Br | H | H | H | NCS |
| 134 | CH$_3$ | H | H | H | H | NHC(=O)NHC(=O)CH$_3$ |
| 135 | CH$_3$ | F | H | H | H | NHC(=O)NHC(=O)CH$_3$ |
| 136 | CH$_3$ | F | F | H | H | NHC(=O)NHC(=O)CH$_3$ |
| 137 | CH$_3$ | Cl | H | H | H | NHC(=O)NHC(=O)CH$_3$ |
| 138 | CH$_3$ | Cl | Cl | H | H | NHC(=O)NHC(=O)CH$_3$ |
| 139 | CH$_3$ | F | F | F | H | NHC(=O)NHC(=O)CH$_3$ |
| 140 | CH$_3$ | Br | H | H | H | NHC(=O)NHC(=O)CH$_3$ |
| 141 | CH$_3$ | H | H | H | H | NHC(=S)NHC(=O)CH$_3$ |
| 142 | CH$_3$ | F | H | H | H | NHC(=S)NHC(=O)CH$_3$ |
| 143 | CH$_3$ | F | F | H | H | NHC(=S)NHC(=O)CH$_3$ |
| 144 | CH$_3$ | Cl | H | H | H | NHC(=S)NHC(=O)CH$_3$ |
| 145 | CH$_3$ | Cl | Cl | H | H | NHC(=S)NHC(=O)CH$_3$ |
| 146 | CH$_3$ | F | F | F | H | NHC(=S)NHC(=O)CH$_3$ |
| 147 | CH$_3$ | Br | H | H | H | NHC(=S)NHC(=O)CH$_3$ |
| 148 (A1a) | CH$_3$ | H | H | H | H | I |
| 149 (A1b) | CH$_3$ | F | H | H | H | I |
| 150 | CH$_3$ | F | F | H | H | I |
| 151 | CH$_3$ | Cl | H | H | H | I |
| 152 | CH$_3$ | Cl | Cl | H | H | I |
| 153 | CH$_3$ | F | F | F | H | I |
| 154 | CH$_3$ | Br | H | H | H | I |
| 155 (B1a) | CH$_3$ | H | H | H | H | 1,2,3-triazol-1-yl |
| 156 (B1b) | CH$_3$ | F | H | H | H | 1,2,3-triazol-1-yl |
| 157 | CH$_3$ | F | F | H | H | 1,2,3-triazol-1-yl |
| 158 | CH$_3$ | Cl | H | H | H | 1,2,3-triazol-1-yl |
| 159 | CH$_3$ | Cl | Cl | H | H | 1,2,3-triazol-1-yl |
| 160 | CH$_3$ | F | F | F | H | 1,2,3-triazol-1-yl |
| 161 | CH$_3$ | Br | H | H | H | 1,2,3-triazol-1-yl. |

8. The method of treatment according to claim 7, wherein the compound is selected from the group consisting of compounds 1-126 and 134-147 in the form of S-enantiomer or a mixture enriched in S-enantiomer.

9. The method of treatment according to claim 7, wherein the compound is selected from the group consisting of compounds 127-133 and 148-161 in the form of R-enantiomer or a mixture enriched in R-enantiomer.

10. The method of treatment according to claim 1, wherein the composition is in the form of tablet, capsule, syrup, or solution administered orally; or the composition is in the form of aqueous or oily solution or emulsion administered parenterally; or the composition is in the form of ointment, cream, gel, solution, O/W or W/O emulsion, suspension emulsion, or suspension administered topically; or the composition is in the form of solution, emulsion, or dispersion administered by inhalation.

11. The method of treatment according to claim 10, wherein the suspension comprises nanoparticles, nanocapsule, liposomes, or a combination thereof.

12. The method of treatment according to claim 11, wherein the nanoparticles are solid lipid nanoparticles that are administered with a nebulizer.

* * * * *